(12) United States Patent
Higuchi et al.

(10) Patent No.: US 8,975,212 B2
(45) Date of Patent: Mar. 10, 2015

(54) PHENOLSULFONIC ACID ARYL ESTER DERIVATIVE, AND HEAT-SENSITIVE RECORDING MATERIAL USING SAME

(75) Inventors: Mai Higuchi, Fukuoka (JP); Yoshimune Aosaki, Tokyo (JP); Keiichiro Inada, Fukuoka (JP); Mamoru Suga, Tokyo (JP); Katsuto Ohse, Tokyo (JP); Yoshimi Midorikawa, Tokyo (JP); Yukiko Sato, Tokyo (JP)

(73) Assignees: Mitsubishi Chemical Corporation, Tokyo (JP); Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 13/822,991

(22) PCT Filed: Sep. 16, 2011

(86) PCT No.: PCT/JP2011/071219
§ 371 (c)(1),
(2), (4) Date: May 6, 2013

(87) PCT Pub. No.: WO2012/036267
PCT Pub. Date: Mar. 22, 2012

(65) Prior Publication Data
US 2013/0237414 A1    Sep. 12, 2013

(30) Foreign Application Priority Data

Sep. 16, 2010 (JP) .................. 2010-208341

(51) Int. Cl.
| | |
|---|---|
| B41M 5/333 | (2006.01) |
| B41M 5/337 | (2006.01) |
| C07C 309/75 | (2006.01) |
| B41M 5/323 | (2006.01) |
| B41M 5/327 | (2006.01) |

(52) U.S. Cl.
CPC ............ B41M 5/3336 (2013.01); C07C 309/75 (2013.01); B41M 5/323 (2013.01); B41M 5/3375 (2013.01); B41M 5/3275 (2013.01); B41M 5/3335 (2013.01)
USPC .............................. 503/216; 503/209; 558/58

(58) Field of Classification Search
CPC ............. B41M 5/3336; B41M 5/3337; B41M 5/3375; C07C 309/75
USPC ...................... 503/209, 216; 558/58
See application file for complete search history.

(56) References Cited

U.S. PATENT DOCUMENTS

| | | | |
|---|---|---|---|
| 4,583,104 A | 4/1986 | Iwakura et al. | |
| 4,792,544 A | 12/1988 | Yamamoto et al. | |
| 4,855,278 A | 8/1989 | Igarashi et al. | |
| 4,999,333 A | 3/1991 | Usami et al. | |
| 6,440,897 B1 * | 8/2002 | Ryu et al. ............. | 503/209 |
| 2004/0241598 A1 | 12/2004 | Suga et al. | |
| 2005/0118526 A1 | 6/2005 | Suga et al. | |
| 2005/0272603 A1 | 12/2005 | Oi et al. | |

FOREIGN PATENT DOCUMENTS

| | | |
|---|---|---|
| CN | 1464843 A | 12/2003 |
| CN | 1561294 A | 1/2005 |
| CN | 1684840 A | 10/2005 |
| EP | 0 699 662 A1 | 3/1996 |
| JP | 60-054884 A | 3/1985 |
| JP | S60-120090 A | 6/1985 |
| JP | 60-176794 A | 9/1985 |
| JP | H01-101188 A | 4/1989 |
| JP | 04-274431 A | 9/1992 |
| JP | 2010-053128 A | 3/2010 |
| WO | 96/08483 A1 | 3/1996 |

OTHER PUBLICATIONS

Cevasco et al., *J. Chem. Soc., Perkin Trans.*, 2: 2215-2218 (1997).
Cevasco et al., *J. Org. Chem.*, 61: 6814-6817 (1996).
Thea et al., *Gazzetta Chimica Italiana*, 117: 705-706 (1987).
Thea et al., *Gazzetta Chimica Italiana*, 126: 7-10 (1996).
Thea et al., *J. Am. Chem. Soc.*, 104: 1128-1129 (1982).
Thea et al., *J. Org. Chem.*, 50: 2158-2165 (1985).
Japanese Patent Office, International Search Report in International Patent Application No. PCT/JP2011/071219 (Oct. 18, 2011).
International Bureau of WIPO, International Preliminary Report in International Patent Application No. PCT/JP2011/071219 (Apr. 9, 2013).
European Patent Office, Extended European Search Report in European Patent Application No. 11825265.9 (Aug. 13, 2014).

* cited by examiner

*Primary Examiner* — Bruce H Hess
(74) *Attorney, Agent, or Firm* — Leydig, Voit & Mayer, Ltd.

(57) ABSTRACT

The invention provides a phenolsulfonic acid aryl ester represented by formula (1)

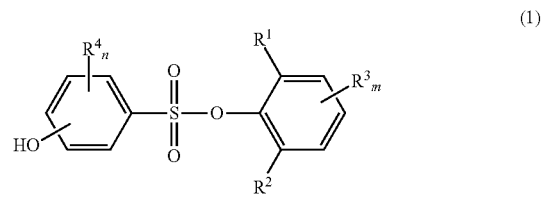

wherein each symbol is as defined in the description. The phenolsulfonic acid aryl ester is useful as a developer to provide a thermal recording material with good color-developing sensitivity, image density when printed at a low application energy (i.e., high start-up sensitivity), and heat and plasticizer resistance. The invention also provides a thermal recording material using the developer.

16 Claims, No Drawings

PHENOLSULFONIC ACID ARYL ESTER DERIVATIVE, AND HEAT-SENSITIVE RECORDING MATERIAL USING SAME

CROSS-REFERENCE TO RELATED APPLICATIONS

This patent application is the U.S. national phase of International Patent Application No. PCT/JP2011/071219, filed on Sep. 16, 2011, which claims the benefit of Japanese Patent Application No. 2010-208341, filed Sep. 16, 2010, which are incorporated by reference in their entireties herein.

TECHNICAL FIELD

The present invention relates to a novel phenolsulfonic acid aryl ester derivative and use thereof as a developer, and a thermal recording material.

BACKGROUND ART

Generally, thermal recording materials having a thermal recording layer based mainly on a colorless or pale-colored basic (electron-donating) leuco dye (hereinafter sometimes to be simply abbreviated as "dye" or "leuco dye") and an electron-accepting developer that develops color by reacting with dye on heating (hereinafter sometimes to be simply abbreviated as "developer") are widely used in practice. For recording on the thermal recording materials, a thermal printer with a built-in thermal head, and the like are used. This method of thermal recording is advantageous over other conventional recording methods in practical use, with features such as (1) noiselessness during recording, (2) obviation of the need for development and fixation, (3) freedom from maintenance work, (4) relatively inexpensive instrumentation, (5) compactness, and (6) very vivid colors developing in the images obtained, and is widely used for facsimiles, computer terminal printers, automated ticket machines, measurement recorders, handy terminals for outdoor use, and the like. When color-developing sensitivity of such thermal recording materials is insufficient, the color-developing sensitivity needs to be increased, since power consumption increases and printing speed decreases.

A factor having a great influence on the color-developing sensitivity is selection of the dye and developer constituting the thermal recording layer, and an influence of the selection of the developer is particularly high.

For example, benzyl p-hydroxybenzoate expected at one time as a high sensitive developer is no longer used at present, since sensitivity is high but image storability is markedly low. In addition, bisphenol A (4,4'-isopropylidenediphenol) is scarcely used in Japan, since color-developing sensitivity is insufficient, image storability such as plasticizer resistance and heat resistance is not satisfactory, and further, environment hormone activity is suspected. To improve these developers, bisphenol S (4,4'-dihydroxydiphenylsulfone) has been put into practice, but it has defects of high melting point and low color-developing sensitivity at low energy application (i.e., start-up sensitivity).

As a developer expected to achieve high sensitivity, a phenolsulfonic acid ester compound disclosed in patent document 1 is substituted at p-position and shows high sensitivity, but is defective in that the storability of blank area and images in the recorded area is low.

The sulfonate compound disclosed in patent document 2 is not a developer but a sensitizer. The compound specifically disclosed in patent document 2 does not have an electron-accepting group and does not show a developing action.

While patent document 3 discloses bis(phenolsulfonic acid) ester compounds, all of the compounds show high storability of images in the recorded area, but the melting point is high and the color-developing sensitivity at low energy application (that is, start-up sensitivity) is low.

DOCUMENT LIST

Patent Documents patent document 1: JP-A-S60-54884
patent document 2: JP-A-S60-176794
patent document 3: JP-A-2010-53128

SUMMARY OF THE INVENTION

Problems to be Solved by the Invention

The demand for a developer to show color development with lower energy application, i.e., start-up sensitivity, is increasing in recent years due to the downsizing of instrument and the like. However, a developer with high start-up sensitivity is inferior in the storability (heat resistance, plasticizer resistance etc.) of blank area and images in the recorded area. When a protection layer is provided on a thermal recording layer in an attempt to improve storability (heat resistance, plasticizer resistance etc.) of blank area and images in the recorded area, the start-up sensitivity becomes particularly inferior since the application energy decreases in the protection layer, and the like, and a developer having both properties is not available.

The present invention aims to provide a novel developer capable of realizing a thermal recording material which shows extremely high color-developing sensitivity, affords good image density (i.e., high start-up sensitivity) even when printed with low energy application, and is superior in storability (heat resistance, plasticizer resistance etc.) of blank area and images in the recorded area, and a thermal recording material using the developer.

Means of Solving the Problems

The present inventors have conducted intensive studies and found that a phenolsulfonic acid aryl ester derivative having a particular structure, that is, a phenolsulfonic acid aryl ester represented by the following formula (1), is superior as a developer, and that a thermal recording material containing the phenolsulfonic acid aryl ester in a thermal recording layer as a developer is a well-balanced thermal recording material which shows extremely high color-developing sensitivity, affords good image density (i.e., high start-up sensitivity) even when printed with low energy application, and shows good in storability (heat resistance, plasticizer resistance etc.) of blank area and images in the recorded area, which resulted in the completion of the present invention.

Accordingly, the present invention provides
[1] a phenolsulfonic acid aryl ester represented by the following formula (1):

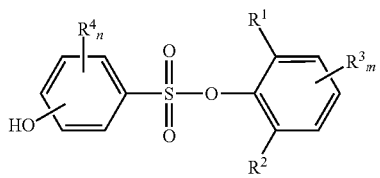

(1)

wherein $R^1$ and $R^2$ are each independently a hydrogen atom, an alkyl group having 1 to 8 carbon atoms, an alkoxy group having 1 to 8 carbon atoms, a halogen atom, a nitro group or a hydroxy group, and $R^1$ and $R^2$ are not simultaneously hydrogen atoms; $R^3$ and $R^4$ are each independently an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms; m is an integer of 0-3; and n is an integer of 0-4,

[2] the phenolsulfonic acid aryl ester of the aforementioned [1], wherein $R^1$ and $R^2$ are each independently an alkyl group having 1 to 8 carbon atoms; and $R^3$ is an alkyl group having 1 to 8 carbon atoms,

[3] the phenolsulfonic acid aryl ester of the aforementioned [1] represented by the following formula (2):

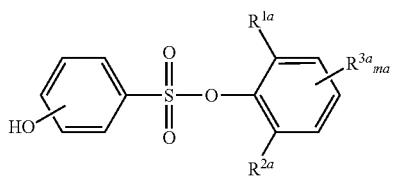

(2)

wherein $R^{1a}$ and $R^{2a}$ are each independently a hydrogen atom, an alkyl group having 1 to 8 carbon atoms, an alkoxy group having 1 to 8 carbon atoms, and $R^{1a}$ and $R^{2a}$ are not simultaneously hydrogen atoms; $R^{3a}$ is an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms; and ma is an integer of 0-3,

[4] the phenolsulfonic acid aryl ester of the aforementioned [3], wherein $R^{1a}$ and $R^{2a}$ are each independently an alkyl group having 1 to 8 carbon atoms; and $R^{3a}$ is an alkyl group having 1 to 8 carbon atoms,

[5] a developer for a thermal recording material, comprising at least one kind of the phenolsulfonic acid aryl ester of any of the aforementioned [1]-[4],

[6] a thermal recording material comprising a support and a thermal recording layer comprising a colorless or pale-colored basic leuco dye and a developer for color development of the basic leuco dye, which layer is laminated on at least one surface of the support, wherein the aforementioned developer contains at least one kind of phenolsulfonic acid aryl ester of any of the aforementioned [1]-[4],

[7] the thermal recording material of the aforementioned [6], wherein the aforementioned developer further contains at least one kind of a second developer selected from the group consisting of a bisphenol compound, a bisphenol sulfone compound, a urea compound and a novolac type phenol compound,

[8] the thermal recording material of the aforementioned [6] or [7], wherein the aforementioned thermal recording layer contains at least one kind of sensitizer selected from the group consisting of 1,2-di-(3-methylphenoxy)ethane, fatty acid amide having 10 to 21 carbon atoms, 3-benzyloxynaphthalene and diphenylsulfone,

[9] the thermal recording material of any of the aforementioned [6]-[8], wherein the aforementioned thermal recording layer contains a hindered phenol compound,

[10] the thermal recording material of the aforementioned [9], wherein the hindered phenol compound is at least one kind m selected from the group consisting of a compound represented by the following formula (3), a compound represented by the following formula (5) and a compound represented by the following formula (6):

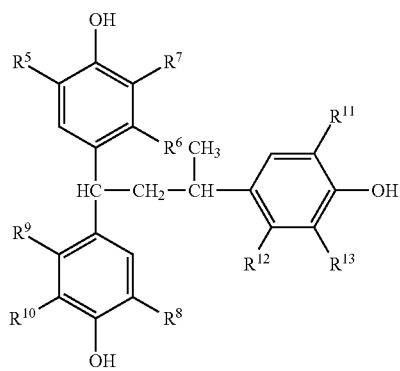

(3)

wherein $R^5$, $R^8$ and $R^{11}$ are each independently an alkyl group having 1 to 8 carbon atoms or a cycloalkyl group having 3 to 8 carbon atoms, $R^6$, $R^7$, $R^9$, $R^{10}$, $R^{12}$ and $R^{13}$ are each independently a hydrogen atom, an alkyl group having 1 to 8 carbon atoms or a cycloalkyl group having 3 to 6 carbon atoms,

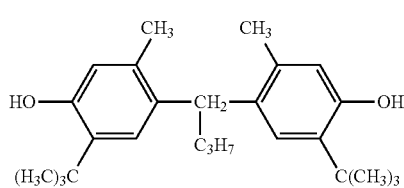

(5)

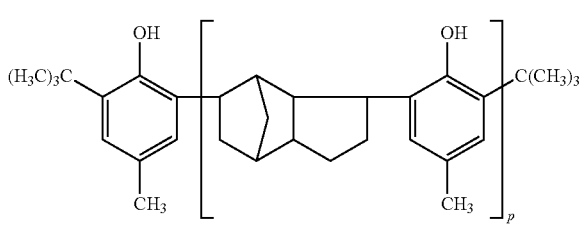

(6)

wherein p is 1 or 2, and

[11] the thermal recording material of the aforementioned [10], wherein the compound represented by the formula (3) is a compound represented by the following formula (4):

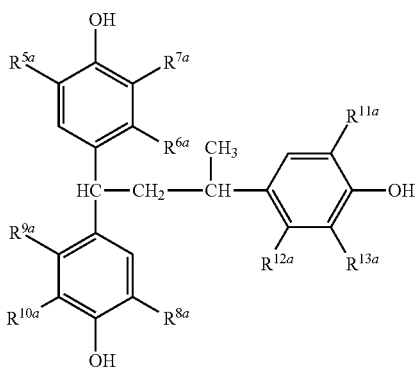

(4)

wherein $R^{5a}$, $R^{8a}$ and $R^{11a}$ are each a tert-butyl group or a cyclohexyl group, $R^{6a}$, $R^{9a}$ and $R^{12a}$ are methyl groups, and $R^{7a}$, $R^{10a}$ and $R^{13a}$ are hydrogen atoms.

Effect of the Invention

According to the present invention, a well-balanced thermal recording material which shows extremely high color-developing sensitivity, affords good image density (i.e., high start-up sensitivity) even when printed with low energy application, and shows good in storability (heat resistance, plasticizer resistance etc.) of blank area and images in the recorded area can be provided by using a novel phenolsulfonic acid aryl ester represented by the formula (1) as a developer for the thermal recording material.

In the present invention, moreover, extremely high start-up sensitivity can be obtained even when a protection layer is provided on a thermal recording layer to particularly improve storability of blank area and images in the recorded area.

DESCRIPTION OF EMBODIMENTS

The present invention is explained in more detail in the following.

The phenolsulfonic acid aryl ester of the present invention is represented by the following formula (1):

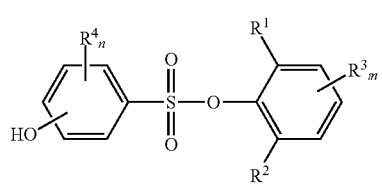

(1)

wherein $R^1$ and $R^2$ are each independently a hydrogen atom, an alkyl group having 1 to 8 carbon atoms, an alkoxy group having 1 to 8 carbon atoms, a halogen atom, a nitro group or a hydroxy group, and $R^1$ and $R^2$ are not simultaneously hydrogen atoms; $R^3$ and $R^4$ are each independently an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms; m is an integer of 0-3; and n is an integer of 0-4.

The definition of each symbol in the above-mentioned formula (1) is described in detail in the following.

In the formula (1), $R^1$ and $R^2$ are each independently a hydrogen atom, an alkyl group having 1 to 8 carbon atoms, an alkoxy group having 1 to 8 carbon atoms, a halogen atom, a nitro group or a hydroxy group, and $R^1$ and $R^2$ are not simultaneously hydrogen atoms. $R^1$ and $R^2$ may be the same or different, preferably the same, but are not simultaneously hydrogen atoms.

The "alkyl group having 1 to 8 carbon atoms" for $R^1$ or $R^2$ may be linear or branched. Examples of such alkyl group include a methyl group, an ethyl group, an n-propyl group, an isopropyl group, an n-butyl group, a t-butyl group, an n-pentyl group, an isopentyl group, a neopentyl group, a t-pentyl group, an n-hexyl group, an isohexyl group, a 1-methylpentyl group, a 2-methylpentyl group and the like. The alkyl group preferably has 1 to 5 carbon atoms, more preferably 1 to 3 carbon atoms.

The "alkoxy group having 1 to 8 carbon atoms" for $R^1$ or $R^2$ may be linear or branched. Examples of such alkoxy group include a methoxy group, an ethoxy group, an n-propoxy group, an isopropoxy group, an n-butoxy group, a t-butoxy group, an n-pentoxy group, an isopentoxy group, a neopentoxy group, a t-pentoxy group, an n-hexyloxy group, an isohexyloxy group and the like. Among these, an alkoxy group having 1 to 4 carbon atoms such as a methoxy group, an ethoxy group, an n-propoxy group, an isopropoxy group and a t-butoxy group are preferable, from the aspects of easy synthesis, easy availability of starting materials and industrialization.

Examples of the "halogen atom" for $R^1$ or $R^2$ include a chlorine atom, a bromine atom, a fluorine atom and an iodine atom. Among these, a chlorine atom and a bromine atom are preferable.

The "alkenyl group having 2 to 8 carbon atoms" for $R^1$ or $R^2$ may be linear or branched and examples thereof include a vinyl group, an allyl group, an isopropenyl group, a 1-propenyl group, a 2-butenyl group, a 3-butenyl group, a 1,3-butanedienyl group, a 2-methyl-2-propenyl group and the like. Among these, a vinyl group and an allyl group are preferable.

Examples of the "aryl group having 6 to 14 carbon atoms" for $R^1$ or $R^2$ include monocyclic-tricyclic aromatic hydrocarbon groups. For example, a phenyl group, a naphthyl group, an anthryl group, a phenanthryl group and the like can be mentioned and, among these, a phenyl group is preferable. The aryl group may be substituted by, for example, the above-mentioned alkyl group, the above-mentioned aryl group, a hydroxy group, a halogen atom, where the substitutable position(s) and the number of the substituents may be any and are not particularly limited. When substituted by two or more substituents, the substituents may be the same or different. In addition, the aryl group may be condensed with a benzene ring bound thereto.

Examples of the "aralkyl group having 7 to 15 carbon atoms" for $R^1$ or $R^2$ include a phenylmethyl group (benzyl group), a phenylethyl group (phenethyl group), a diphenylmethyl group, a 3-phenylpropyl group, a 2-phenylpropyl group, a 4-phenylbutyl group, a biphenyl group, a biphenylmethyl group, a naphthylmethyl group and the like. Among these, an aralkyl group having 7 or 8 carbon atoms such as a benzyl group is preferable.

$R^1$ and $R^2$ are preferably each independently a hydrogen atom, an alkyl group having 1 to 8 carbon atoms or an alkoxy group having 1 to 8 carbon atoms, and $R^1$ and $R^2$ are not simultaneously hydrogen atoms.

$R^3$ and $R^4$ are each independently an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms.

Examples of the "alkyl group having 1 to 8 carbon atoms", "alkenyl group having 2 to 8 carbon atoms", "alkoxy group having 1 to 8 carbon atoms", "halogen atom", "aryl group having 6 to 14 carbon atoms" and "aralkyl group having 7 to 15 carbon atoms" for $R^3$ or $R^4$ include those similar to the "alkyl group having 1 to 8 carbon atoms", "alkenyl group having 2 to 8 carbon atoms", "alkoxy group having 1 to 8 carbon atoms", "halogen atom", "aryl group having 6 to 14 carbon atoms" and "aralkyl group having 7 to 15 carbon atoms", respectively, for the above-mentioned $R^1$ or $R^2$.

$R^3$ and $R^4$ are preferably each independently alkyl having 1 to 8 carbon atoms, particularly preferably a methyl group or an ethyl group.

In the formula (1), m is an integer of 0-3, preferably an integer of 0-2, particularly preferably 0 or 1, and n is an integer of 0-4, preferably an integer of 0-2, particularly preferably 0 or 1.

The phenolsulfonic acid aryl ester represented by the formula (1) is preferably a compound wherein $R^1$ and $R^2$ are each independently a hydrogen atom, an alkyl group having 1 to 8 carbon atoms, or an alkoxy group having 1 to 8 carbon atoms, and $R^1$ and $R^2$ are not simultaneously hydrogen atoms;

$R^3$ and $R^4$ are each independently an alkyl group having 1 to 8 carbon atoms (preferably a methyl group or an ethyl group);

m is an integer of 0-2 (preferably 0 or 1); and n is an integer of 0-2 (preferably 0 or 1).

In the present invention, of the phenolsulfonic acid aryl esters represented by the formula (1), one represented by the following formula (2) is particularly preferable:

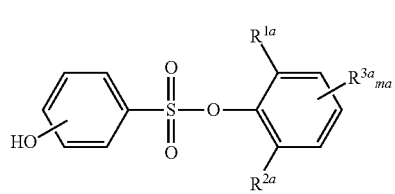

(2)

wherein $R^{1a}$ and $R^{2a}$ are each independently a hydrogen atom, an alkyl group having 1 to 8 carbon atoms, an alkoxy group having 1 to 8 carbon atoms, and $R^{1a}$ and $R^{2a}$ are not simultaneously hydrogen atoms; $R^{3a}$ is an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms; and ma is an integer of 0-3.

The definition of each symbol in the above-mentioned formula (2) is described in detail in the following.

In the formula (2), $R^{1a}$ and $R^{2a}$ are each independently a hydrogen atom, an alkyl group having 1 to 8 carbon atoms, an alkoxy group having 1 to 8 carbon atoms, and $R^{1a}$ and $R^{2a}$ are not simultaneously hydrogen atoms. In addition, $R^{1a}$ and $R^{2a}$ may be the same or different and preferably the same, but are not simultaneously hydrogen atoms.

The "alkyl group having 1 to 8 carbon atoms" for $R^{1a}$ or $R^{2a}$ may be linear or branched. Examples of such alkyl group include a methyl group, an ethyl group, an n-propyl group, an isopropyl group, an n-butyl group, a t-butyl group, an n-pentyl group, an isopentyl group, a neopentyl group, a t-pentyl group, an n-hexyl group, an isohexyl group, a 1-methylpentyl group, a 2-methylpentyl group and the like. The alkyl group preferably has 1 to 5 carbon atoms, more preferably 1 to 3 carbon atoms.

The "alkoxy group having 1 to 8 carbon atoms" for $R^{1a}$ or $R^{2a}$ may be linear or branched. Examples of such alkoxy group include a methoxy group, an ethoxy group, an n-propoxy group, an isopropoxy group, an n-butoxy group, a t-butoxy group and the like. Among these, an alkoxy group having 1 to 4 carbon atoms such as a methoxy group, an ethoxy group, an n-propoxy group, an isopropoxy group and a t-butoxy group is preferable from the aspects of easy synthesis, easy availability of starting materials and industrialization.

$R^{1a}$ and $R^{2a}$ are preferably each independently a hydrogen atom, a methyl group, an ethyl group, an n-propyl group, an isopropyl group, a methoxy group or an ethoxy group. Of these, $R^{1a}$ and $R^{2a}$ are preferably each independently a methyl group or an ethyl group, particularly preferably both $R^{1a}$ and $R^{2a}$ are methyl groups or ethyl groups.

$R^{3a}$ is an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms.

Examples of the "alkyl group having 1 to 8 carbon atoms", "alkenyl group having 2 to 8 carbon atoms", "alkoxy group having 1 to 8 carbon atoms", "halogen atom", "aryl group having 6 to 14 carbon atoms" and "aralkyl group having 7 to 15 carbon atoms" for $R^{3a}$ include those similar to the "alkyl group having 1 to 8 carbon atoms", "alkenyl group having 2 to 8 carbon atoms", "alkoxy group having 1 to 8 carbon atoms", "halogen atom", "aryl group having 6 to 14 carbon atoms" and "aralkyl group having 7 to 15 carbon atoms", respectively, for the above-mentioned $R^1$ or $R^2$.

$R^{3a}$ is preferably an "alkyl group having 1 to 8 carbon atoms", particularly preferably a methyl group or an ethyl group.

In the formula (2), ma is an integer of 0-3, preferably an integer of 0-2, particularly preferably 0 or 1.

When ma is 1, the 4-position of the benzene ring (para-position to sulfonyl group) is preferably substituted by $R^{3a}$.

In the formula (2), the 4-position of the benzene ring (para-position to sulfonyl group) is preferably substituted by a hydroxyl group.

Preferred as the phenolsulfonic acid aryl ester represented by the formula (2) is a compound wherein $R^{1a}$ and $R^{2a}$ are each independently a hydrogen atom, a methyl group, an ethyl group, an n-propyl group, an isopropyl group, a methoxy group or an ethoxy group (preferably, methyl group or ethyl group), and $R^1$ and $R^2$ are not simultaneously hydrogen atoms;

$R^{3a}$ is an alkyl group having 1 to 8 carbon atoms (preferably, methyl group or ethyl group); and ma is an integer of 0-2 (preferably 0 or 1).

Preferable examples of the phenolsulfonic acid aryl ester represented by the above-mentioned formula (1) or (2) in the present invention include, but are not limited to, the compounds represented by the following formulas (a1)-(a11). In the following, the "compound represented by the formula (a1)" and the like are sometimes to be abbreviated as "exemplary compound (a1)" and the like.

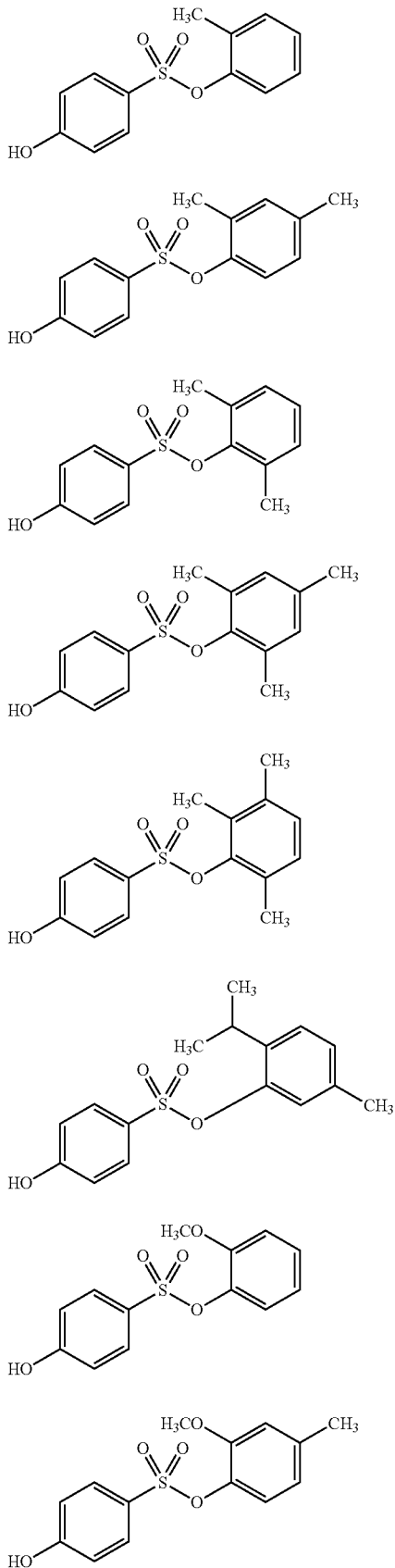

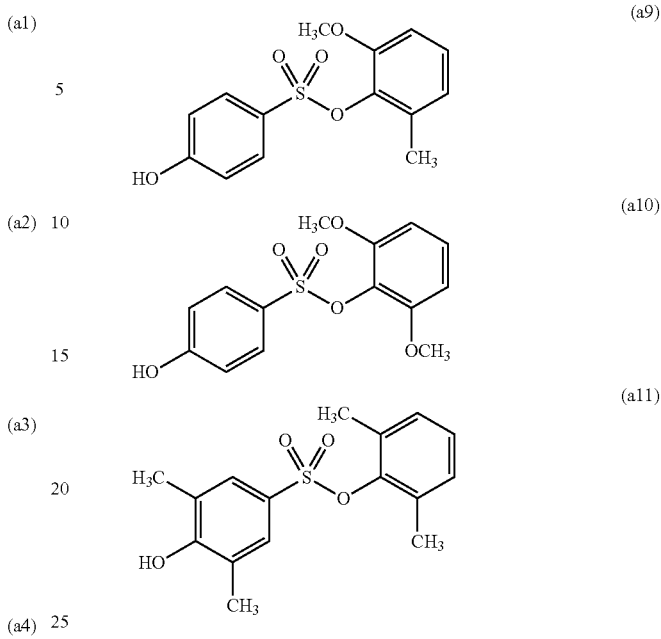

Of these, exemplary compounds (a3)-(a8) are preferable from the aspect of the balance of color-developing sensitivity and storability.

The phenolsulfonic acid aryl ester of the present invention is synthesized according to a known production method of sulfonic acid ester. For example, as described in the aforementioned patent document 3, acetoxybenzenesulfonyl chloride and phenol derivative are reacted to give an ester, which is then deacetylated under basic conditions or acidic conditions to give the object product.

The developer for thermal recording material of the present invention contains at least one kind of the phenolsulfonic acid aryl ester represented by the above-mentioned formula (1). While the developer for thermal recording material of the present invention may contain components other than the phenolsulfonic acid aryl ester represented by the above-mentioned formula (1), the content of the phenolsulfonic acid aryl ester represented by the above-mentioned formula (1) is 80 wt % or more at the minimum, preferably 90 wt % or more, particularly preferably 95 wt % or more.

The thermal recording material of the present invention has a thermal recording layer laminated on at least one surface of a support, and the thermal recording layer contains at least one kind of the phenolsulfonic acid aryl ester represented by the above-mentioned formula (1) as a developer.

Various materials to be used for the thermal recording layer of the present invention are exemplified in the following.

[Second Developer]

The thermal recording layer of the present invention can contain, as a developer, the phenolsulfonic acid aryl ester represented by the above-mentioned formula (1) and other developer (hereinafter to be also simply referred to as "the second developer").

The content of the second developer in the thermal recording layer of the present invention is generally 0.005-1 part by weight, preferably 0.01-0.8 parts by weight, particularly preferably 0.02-0.7 parts by weight, relative to 1 part by weight of the phenolsulfonic acid aryl ester in the present invention. When the content of the second developer is within such range, a thermal recording material superior in image storability such as water resistance and moisture resistance, which maintains high color-developing sensitivity, can be obtained.

As the second developer in the present invention, any which is conventionally known in the field of pressure sensitive or thermal recording paper can be used, and is not particularly limited. Preferred are a bisphenolsulfone compound, a bisphenol compound, a urea compound and a novolac type phenol compound. Specific examples of the representative developer are as follows.

<Bisphenolsulfone Compound>

4,4'-dihydroxydiphenylsulfone, 2,4'-dihydroxydiphenylsulfone, 4-hydroxy-4'-n-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, 4-hydroxyphenyl-4'-benzyloxyphenylsulfone, 3,4-dihydroxyphenyl-4'-methylphenylsulfone, bisphenolsulfone crosslinking type compound described in JP-B-3913820, bisphenolsulfone derivative compound described in JP-B-4004289, and the like <Bisphenol Compound>

4,4'-isopropylidenediphenol, 2,2'-bis(4-hydroxy-3-methylphenyl)propane, 1,1-bis(4-hydroxyphenyl)cyclohexane, 2,2-bis(4-hydroxyphenyl)-4-methylpentane, 4,4'-dihydroxydiphenylsulfide, di(4-hydroxy-3-methylphenyl)sulfide, 2,2'-thiobis(3-tert-octylphenol), 2,2'-thiobis(4-tert-octylphenol) and the like <Urea Compound>

4,4'-bis(3-(phenoxycarbonylamino)methylphenylureido) diphenylsulfone, a N-(p-toluenesulfonyl)-N'-(3-p-toluenesulfonyl-oxy-phenyl)urea compound described in JP-B-4601174, and the like <Novolac Type Phenol Compound> phenol-formalin condensation product described in WO02/098674, and the like

<Others> inorganic acidic substances such as activated clay, attapulgite, colloidal silica, aluminum silicate, hydroquinone monobenzyl ether, benzyl 4-hydroxybenzoate, aminobenzenesulfoneamide derivative described in JP-A-H08-59603, bis(4-hydroxyphenylthioethoxy)methane, 1,5-di(4-hydroxyphenylthio)-3-oxapentane, bis(p-hydroxyphenyl)butyl acetate, bis(p-hydroxyphenyl)methyl acetate, 1,1-bis(4-hydroxyphenyl)-1-phenylethane, 1,4-bis[α-methyl-α-(4'-hydroxyphenyl)ethyl]benzene, 1,3-bis[α-methyl-α-(4'-hydroxyphenyl)ethyl]benzene, compound described in WO02/081229 or JP-A-2002-301873, thiourea compounds such as N,N'-di-m-chlorophenylthiourea; aromatic carboxylic acids such as p-chlorobenzoic acid, stearyl gallate, bis[4-(n-octyloxycarbonylamino) zinc salicylate]dihydrate, 4-[2-(p-methoxyphenoxy)ethyloxy]salicylic acid, 4-[3-(p-tolylsulfonyl)propyloxy]salicylic acid, 5-[p-(2-p-methoxyphenoxyethoxy)cumyl]salicylic acid and salts of these aromatic carboxylic acid with a polyvalent metal salts such as zinc, magnesium, aluminum, calcium, titanium, manganese and tin nickel; zinc thiocyanate antipyrine complex; composite zinc salt of terephthalaldehyde acid and other aromatic carboxylic acid, and the like. Metal chelate type color developing components such as higher fatty acid metal double salt described in JP-A-H10-258577, polyvalent hydroxyaromatic compound and the like can also be contained.

Of these second developers, preferred are 4,4'-dihydroxydiphenylsulfone, 2,4'-dihydroxydiphenylsulfone, 4-hydroxy-4'-n-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, 4,4'-isopropylidenediphenol, 2,2'-bis(4-hydroxy-3-methylphenyl)propane, diphenylsulfone crosslinking type compound described in JP-B-3913820, diphenylsulfone derivative compound described in JP-B-4004289, phenol-formalin condensation product described in WO02/098674, 4,4'-bis(3-(phenoxycarbonylamino)methylphenylureido) diphenylsulfone, and N-(p-toluenesulfonyl)-N'-(3-p-toluenesulfonyl-oxy-phenyl)urea compound described in JP-B-4601174, particularly preferred are 4,4'-dihydroxydiphenylsulfone, 2,4'-dihydroxydiphenylsulfone, 4-hydroxy-4'-n-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, bisphenolsulfone crosslinking type compound described in JP-B-3913820, and bisphenolsulfone derivative compound described in JP-B-4004289. These second developers can also used alone, or two or more kinds thereof may be used in a mixture. These compounds can be produced by a known method.

[Colorless or Pale-Colored Basic (Electron-Donating) Leuco Dye]

As the colorless or pale-colored basic (electron-donating) leuco dye to be used in the present invention, all of those conventionally known in the field of pressure sensitive or thermal recording paper can be used. Although it is not particularly limited, triphenylmethane compounds, fluoran compounds, fluorene compounds, divinyl compounds and the like are preferable. Specific examples of the representative leuco dye (dye precursor) are shown below. These dye precursors may be used alone or two or more kinds thereof may be combined.

<Triphenylmethane Leuco Dye>

3,3-bis(p-dimethylaminophenyl)-6-dimethylaminophthalide [aka crystal violet lactone], 3,3-bis(p-dimethylaminophenyl)phthalide [aka malachite green lactone]

<Fluoran Leuco Dye>

3-diethylamino-6-methylfluoran,
3-diethylamino-6-methyl-7-anilinofluoran,
3-diethylamino-6-methyl-7-(o,p-dimethylanilino)fluoran,
3-diethylamino-6-methyl-7-chlorofluoran,
3-diethylamino-6-methyl-7-(m-trifluoromethylanilino)fluoran,
3-diethylamino-6-methyl-7-(o-chloroanilino)fluoran,
3-diethylamino-6-methyl-7-(p-chloroanilino)fluoran,
3-diethylamino-6-methyl-7-(o-fluoroanilino)fluoran,
3-diethylamino-6-methyl-7-(m-methylanilino)fluoran,
3-diethylamino-6-methyl-7-n-octylanilinofluoran,
3-diethylamino-6-methyl-7-n-octylaminofluoran,
3-diethylamino-6-methyl-7-benzylaminofluoran,
3-diethylamino-6-methyl-7-dibenzylaminofluoran,
3-diethylamino-6-chloro-7-methylfluoran,
3-diethylamino-6-chloro-7-anilinofluoran,
3-diethylamino-6-chloro-7-p-methylanilinofluoran,
3-diethylamino-6-ethoxyethyl-7-anilinofluoran,
3-diethylamino-7-methylfluoran,
3-diethylamino-7-chlorofluoran,
3-diethylamino-7-(m-trifluoromethylanilino)fluoran,
3-diethylamino-7-(o-chloroanilino)fluoran,
3-diethylamino-7-(p-chloroanilino)fluoran,
3-diethylamino-7-(o-fluoroanilino)fluoran,
3-diethylamino-benzo[a]fluoran,
3-diethylamino-benzo[c]fluoran,
3-dibutylamino-6-methyl-fluoran,
3-dibutylamino-6-methyl-7-anilinofluoran,
3-dibutylamino-6-methyl-7-(o,p-dimethylanilino)fluoran,
3-dibutylamino-6-methyl-7-(o-chloroanilino)fluoran,
3-dibutylamino-6-methyl-7-(p-chloroanilino)fluoran,
3-dibutylamino-6-methyl-7-(o-fluoroanilino)fluoran, 3-dibutylamino-6-methyl-7-(m-trifluoromethylanilino)fluoran,
3-dibutylamino-6-methyl-chlorofluoran,
3-dibutylamino-6-ethoxyethyl-7-anilinofluoran,
3-dibutylamino-6-chloro-7-anilinofluoran,
3-dibutylamino-6-methyl-7-p-methylanilinofluoran,
3-dibutylamino-7-(o-chloroanilino)fluoran,
3-dibutylamino-7-(o-fluoroanilino)fluoran,
3-di-n-pentylamino-6-methyl-7-anilinofluoran,
3-di-n-pentylamino-6-methyl-7-(p-chloroanilino)fluoran,
3-di-n-pentylamino-7-(m-trifluoromethylanilino)fluoran,
3-di-n-pentylamino-6-chloro-7-anilinofluoran,
3-di-n-pentylamino-7-(p-chloroanilino)fluoran,
3-pyrrolidino-6-methyl-7-anilinofluoran,
3-piperidino-6-methyl-7-anilinofluoran,
3-(N-methyl-N-propylamino)-6-methyl-7-anilinofluoran,
3-(N-methyl-N-cyclohexylamino)-6-methyl-7-anilinofluoran,
3-(N-ethyl-N-cyclohexylamino)-6-methyl-7-anilinofluoran,
3-(N-ethyl-N-cyclohexylamino)-6-methyl-7-(p-chloroanilino)fluoran,
3-(N-ethyl-p-toluidino)-6-methyl-7-anilinofluoran,
3-(N-ethyl-N-isoamylamino)-6-methyl-7-anilinofluoran,
3-(N-ethyl-N-isoamylamino)-6-chloro-7-anilinofluoran,
3-(N-ethyl-N-tetrahydrofurfurylamino)-6-methyl-7-anilinofluoran,
3-(N-ethyl-N-isobutylamino)-6-methyl-7-anilinofluoran,
3-(N-ethyl-N-ethoxypropylamino)-6-methyl-7-anilinofluoran,
3-cyclohexylamino-6-chlorofluoran,
2-(4-oxahexyl)-3-dimethylamino-6-methyl-7-anilinofluoran,
2-(4-oxahexyl)-3-diethylamino-6-methyl-7-anilinofluoran,
2-(4-oxahexyl)-3-dipropylamino-6-methyl-7-anilinofluoran,
2-methyl-6-p-(p-dimethylaminophenyl)aminoanilinofluoran,
2-methoxy-6-p-(p-dimethylaminophenyl)aminoanilinofluoran,
2-chloro-3-methyl-6-p-(p-phenylaminophenyl)aminoanilinofluoran,
2-chloro-6-p-(p-dimethylaminophenyl)aminoanilinofluoran,
2-nitro-6-p-(p-diethylaminophenyl)aminoanilinofluoran,
2-amino-6-p-(p-diethylaminophenyl)aminoanilinofluoran,
2-diethylamino-6-p-(p-diethylaminophenyl)aminoanilinofluoran,
2-phenyl-6-methyl-6-p-(p-phenylaminophenyl)aminoanilinofluoran,
2-benzyl-6-p-(p-phenylaminophenyl)aminoanilinofluoran,
2-hydroxy-6-p-(p-phenylaminophenyl)aminoanilinofluoran,
3-methyl-6-p-(p-dimethylaminophenyl)aminoanilinofluoran,
3-diethylamino-6-p-(p-diethylaminophenyl)aminoanilinofluoran,
3-diethylamino-6-p-(p-dibutylaminophenyl)aminoanilinofluoran,
2,4-dimethyl-6-[(4-dimethylamino)anilino]-fluoran.
<Fluorene Leuco Dye>
3,6,6'-tris(dimethylamino)spiro[fluorene-9,3'-phthalide],
3,6,6'-tris(diethylamino)spiro[fluorene-9,3'-phthalide].
<Divinyl Leuco Dye>
3,3-bis-[2-(p-dimethylaminophenyl)-2-(p-methoxyphenyl)ethenyl]-4,5,6,7-tetrabromophthalide,
3,3-bis-[2-(p-dimethylaminophenyl)-2-(p-methoxyphenyl)ethenyl]-4,5,6,7-tetrachlorophthalide,
3,3-bis-[1,1-bis(4-pyrrolidinophenyl)ethylen-2-yl]-4,5,6,7-tetrabromophthalide,
3,3-bis-[1-(4-methoxyphenyl)-1-(4-pyrrolidinophenyl)ethylen-2-yl]-4,5,6,7-tetrachlorophthalide.
<Others>
3-(4-diethylamino-2-ethoxyphenyl)-3-(1-ethyl-2-methylindol-3-yl)-4-azaphthalide,
3-(4-diethylamino-2-ethoxyphenyl)-3-(1-octyl-2-methylindol-3-yl)-4-azaphthalide,
3-(4-cyclohexylethylamino-2-methoxyphenyl)-3-(1-ethyl-2-methylindol-3-yl)-4-azaphthalide,
3,3-bis(1-ethyl-2-methylindol-3-yl)phthalide,
3,6-bis(diethylamino)fluoran-γ-(3'-nitro)anilinolactam,
3,6-bis(diethylamino)fluoran-γ-(4'-nitro)anilinolactam,
1,1-bis-[2',2',2'',2''-tetrakis-(p-dimethylaminophenyl)-ethenyl]-2,2-dinitrileethane,
1,1-bis-[2',2',2'',2''-tetrakis-(p-dimethylaminophenyl)-ethenyl]-2-β-naphthoylethane,
1,1-bis-[2',2',2'',2''-tetrakis-(p-dimethylaminophenyl)-ethenyl]-2,2-diacetylethane,
bis-[2,2,2',2'-tetrakis-(p-dimethylaminophenyl)-ethenyl]-methylmalonic acid dimethyl ester.

[Sensitizer]

As the sensitizer to be used in the present invention, any conventionally-known sensitizers can be used and is not particularly limited. For example, fatty acid amide having 10 to 21 carbon atoms such as stearic acid amide and palmitic acid amide, ethylenebisamide, montanic acid wax, polyethylene wax, 1,2-di-(3-methylphenoxy)ethane, p-benzylbiphenyl, β-benzyloxynaphthalene, diphenylsulfone, 4-biphenyl-p-tolylether, m-terphenyl, 1,2-diphenoxyethane, dibenzyl oxalate, di(p-chlorobenzyl) oxalate, di(p-methylbenzyl) oxalate, dibenzyl terephthalate, benzyl p-benzyloxybenzoate, di-p-tolyl carbonate, phenyl α-naphthylcarbonate, 1,4-diethoxynaphthalene, 1-hydroxy-2-naphthoic acid phenyl ester, o-xylene-bis-(phenylether), 4-(m-methylphenoxymethyl)biphenyl, 4,4'-ethylenedioxy-bis-benzoic acid dibenzyl ester, dibenzoyloxymethane, 1,2-di(3-methylphenoxy)ethylene, bis[2-(4-methoxy-phenoxy)ethyl]ether, methyl p-nitrobenzoate and phenyl p-toluenesulfonate can be used. Of these, particularly preferred are fatty acid amide having 10 to 21 carbon atoms such as 1,2-di-(3-methylphenoxy)ethane, stearic acid amide and palmitic acid amide, β-benzyloxynaphthalene, and diphenylsulfone. These sensitizers may be used alone, or two or more kinds thereof may be used in a mixture. These sensitizers may not be used.

[Stabilizer]

In the present invention, a stabilizer can be used as long as it does not inhibit the desired effect on the above-mentioned problems, to improve storability of blank area and images in the recorded area, and the like. Examples of such stabilizer include, but are not particularly limited to, hindered phenol compound, 4,4'-butylidene(6-t-butyl-3-methylphenol), 2,2'-di-t-butyl-5,5'-dimethyl-4,4'-sulfonyldiphenol, 1,1,3-tris(2-methyl-4-hydroxy-5-cyclohexylphenyl)butane, 1,1,3-tris(2-methyl-4-hydroxy-5-t-butylphenyl)butane and the like, or benzophenone or triazole UV absorber. These stabilizers may be used alone, or two or more kinds thereof may be used in a mixture. Of these, particularly preferred is a hindered phenol compound.

<Hindered Phenol Compound>

The hindered phenol compound to be used in the present invention has, in one molecule, generally not less than 1 and not more than 15, preferably not less than 2 and not more than 6, phenol groups. The compound generally has a molecular weight of not less than 200 and not more than 2000, preferably not less than 250 and not more than 1800, more preferably not less than 300 and not more than 1500.

The melting point of the hindered phenol compound to be used in the present invention is preferably 100° C. or more and generally 300° C. or less.

The hindered phenol compound to be used in the present invention preferably has at least one phenol group wherein one of the 2-position and the 6-position is a hydrogen atom (hydroxyphenyl group).

Examples of preferable embodiment of the hindered phenol compound to be used in the present invention include tris(hydroxyphenyl)alkane, 1,1,3-tris-substituted butane compound and the like, specifically tris(hydroxyphenyl)alkane, a 1,1,3-tris-substituted butane compound and the like described in JP-B-S39-4469, JP-A-S56-40629 and the like.

In the present invention, the hindered phenol compound is particularly preferably tris(hydroxyphenyl)alkane or a 1,1,3-tris-substituted butane compound, especially preferably a compound represented by the following formula (3) (hereinafter to be also referred to as the compound of the formula (3)), to improve storability:

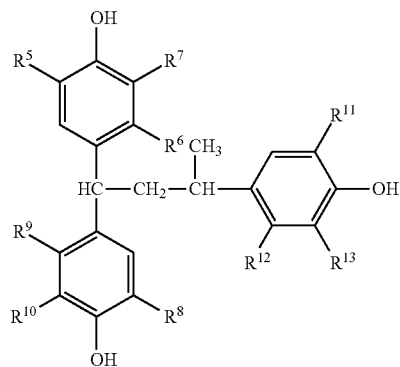

(3)

wherein $R^5$, $R^8$ and $R^{11}$ are each independently an alkyl group having 1 to 8 carbon atoms or a cycloalkyl group having 3 to 8 carbon atoms, and $R^6$, $R^7$, $R^9$, $R^{10}$, $R^{12}$ and $R^{13}$ are each independently a hydrogen atom, an alkyl group having 1 to 8 carbon atoms or a cycloalkyl group having 3 to 5 carbon atoms.

In the compound of the formula (3), the "alkyl group having 1 to 8 carbon atoms" for $R^5$, $R^8$ or $R^{11}$ may be linear or branched. Specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, an n-hexyl group, an isohexyl group, a sec-hexyl group, a tert-hexyl group, a heptyl group, an n-octyl group, an isooctyl group, a sec-octyl group, a tert-octyl group, a 2-ethylhexyl group and the like. The alkyl group preferably has 1 to 6 carbon atoms.

In the compound of the formula (3), the "cycloalkyl group having 3 to 8 carbon atoms" for $R^5$, $R^8$ or $R^{11}$ is exemplified by a cyclopropyl group, a cyclobutyl group, a cyclopentyl group, a cyclohexyl group and the like. The cycloalkyl group preferably has 3 to 6 carbon atoms.

In the compound of the formula (3), $R^5$, $R^8$ and $R^{11}$ may be the same group or different groups, preferably the same group with each other.

In the compound of the formula (3), the "alkyl group having 1 to 8 carbon atoms" for $R^6$, $R^7$, $R^9$, $R^{10}$, $R^{12}$ or $R^{13}$ may be linear or branched. Specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, an n-hexyl group, an isohexyl group, a sec-hexyl group, a tert-hexyl group, a heptyl group, an n-octyl group, an isooctyl group, a sec-octyl group, a tert-octyl group, a 2-ethylhexyl group and the like. The alkyl group preferably has 1 to 5 carbon atoms.

In the compound of the formula (3), the "cycloalkyl group having 3 to 8 carbon atoms" for $R^6$, $R^7$, $R^9$, $R^{10}$, $R^{12}$ or $R^{13}$ is exemplified by a cyclopropyl group, a cyclobutyl group, a cyclopentyl group, a cyclohexyl group and the like. The cycloalkyl group preferably has 3 to 5 carbon atoms.

In the compound of the formula (3), $R^6$, $R^7$, $R^9$, $R^{10}$, $R^{12}$ and $R^{13}$ are each preferably independently a hydrogen atom, an alkyl group having 1 to 5 carbon atoms or a cycloalkyl group having 3 to 5 carbon atoms, and at least one of $R^7$, $R^{10}$ and $R^{13}$ is more preferably a hydrogen atom.

Among the compounds of the formula (3), a compound represented by the following formula (4) (hereinafter to be also referred to as the compound of the formula (4)) is particularly preferable.

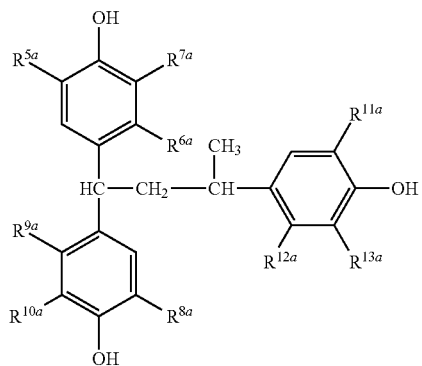

(4)

wherein $R^{5a}$, $R^{8a}$ and $R^{11a}$ are each a tert-butyl group or a cyclohexyl groups, $R^{6a}$, $R^{9a}$ and $R^{12a}$ are methyl groups, and $R^{7a}$, $R^{10a}$ and $R^{13a}$ are hydrogen atoms.

In the compound of the formula (4), $R^{5a}$, $R^{8a}$ and $R^{11a}$ may be the same group with each other or different groups, preferably the same group with each other.

The compounds of the formulas (3) and (4) can be synthesized according to a production method known per se. In addition, the compounds of the formulas (3) and (4) may be commercially available products. Examples of the commercially available product of the compound of the formula (4) wherein $R^{5a}$, $R^{8a}$ and $R^{11a}$ are tert-butyl groups include ADEKA STAB AO-30 (trade name) manufactured by ADEKA CORPORATION, OS-930 (trade name) manufactured by OSAKA SHINYAKU CO., LTD. and the like. Examples of the commercially available product of the compound of the formula (4) wherein $R^{5a}$, $R^{8a}$ and $R^{11a}$ are cyclohexyl groups include ADEKA ARKLS DH-43 (trade name) manufactured by ADEKA CORPORATION and the like.

As the hindered phenol compound, moreover, the compounds represented by the following formulas (5)-(11) can also be used. These compounds can be produced by a known method.
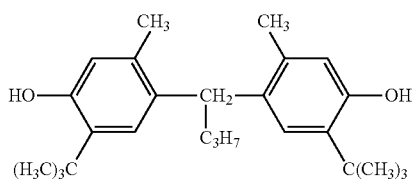
(5)
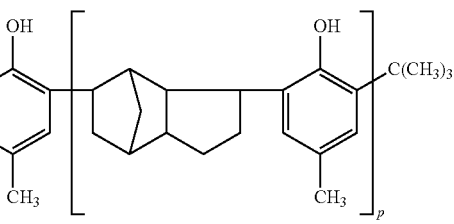
(6)
wherein p is 1 or 2.
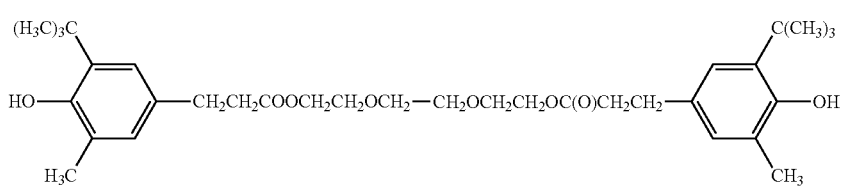
(7)
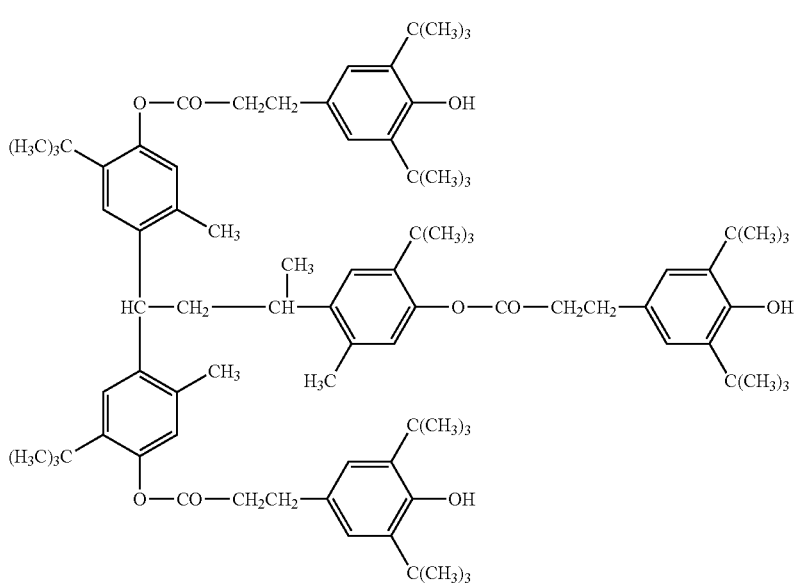
(8)
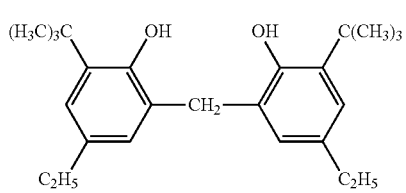
(9)
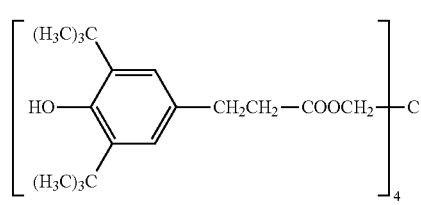
(10)
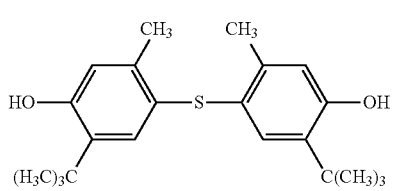
(11)

Of these, at least one kind selected from the group consisting of the compound represented by the following formula (4), the compound represented by the following formula (5) and the compound represented by the following formula (6) can be preferably used.

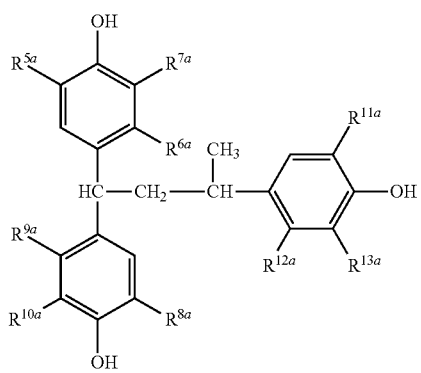

(4)

wherein $R^{5a}$, $R^{8a}$ and $R^{11a}$ are tert-butyl groups or cyclohexyl groups, $R^{6a}$, $R^{9a}$ and $R^{12a}$ are methyl groups, and $R^{7a}$, $R^{10a}$ and $R^{13a}$ are hydrogen atoms,

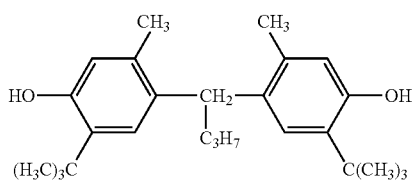

(5)

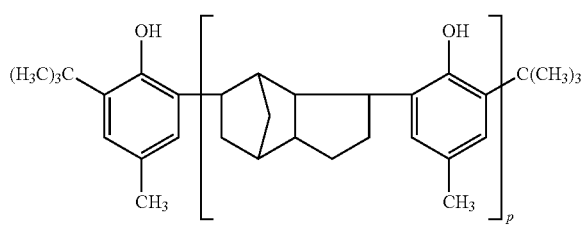

(6)

wherein p is 1 or 2.

In the present invention, any one kind of the hindered phenol compound may be used alone, or two or more kinds thereof may be used in a mixture.

In the thermal recording material of the present invention, the content of the hindered phenol compound in the thermal recording layer is 0.001-2 parts by weight, preferably 0.005-1 part by weight, particularly preferably 0.01-0.5 parts by weight, relative to 1 part by weight of the phenolsulfonic acid aryl ester. When the content of the hindered phenol compound is less than such range, the effect afforded by the use thereof may be insufficient. When it is more than such range, color-developing sensitivity and resistance to plasticizer of images in the recorded area may decrease.

[Other Components]

In the present invention, binder, crosslinking agent, pigment, lubricant, other auxiliary agents and the like can also be used as other components for the thermal recording layer as long as they do not inhibit the desired effect on the above-mentioned problems. In addition, binder, crosslinking agent, pigment, lubricant, other auxiliary agents and the like can be used not only for the thermal recording layer but also for each coating layer provided as necessary such as protection layer.

<Binder>

Examples of the binder to be used in the present invention include completely saponified polyvinyl alcohol, partially saponified polyvinyl alcohol, acetoacetyl polyvinyl alcohol, carboxy-modified polyvinyl alcohol, amide-modified polyvinyl alcohol, sulfonic acid-modified polyvinyl alcohol, butyral-modified polyvinyl alcohol, olefin-modified polyvinyl alcohol, nitrile-modified polyvinyl alcohol, pyrrolidone-modified polyvinyl alcohol, silicone-modified polyvinyl alcohol, other modified polyvinyl alcohols, cellulose derivatives such as hydroxyethyl cellulose, methyl cellulose, ethyl cellulose, carboxymethyl cellulose, styrene-maleic anhydride copolymer, styrene-butadiene copolymer, ethylcellulose, and acetylcellulose, casein, gum arabic, oxidized starch, etherified starch, dialdehyde starch, esterified starch, polyvinyl chloride, polyvinyl acetate, polyacrylamide, polyacrylic acid ester, polyvinyl butyral, polystyrol and their copolymers, polyamide resin, silicone resin, petroleum resin, terpene resin, ketone resin, cumarone resin and the like. These polymer substances are used by dissolving in solvents such as water, alcohol, ketones, esters and hydrocarbon, or used after dispersing in water or other medium to form emulsion or paste, and can be used in combination depending on the request quality.

<Crosslinking Agent>

Examples of the crosslinking agent to be used in the present invention include glyoxal, methylolmelamine, melamine formaldehyde resin, melamine urea resin, polyamine epichlorohydrin resin, polyamide epichlorohydrin resin, potassium persulfate, ammonium persulfate, sodium persulfate, ferric chloride, magnesium chloride, borax, boric acid, alum, ammonium chloride and the like.

<Pigment>

Examples of the pigment to be used in the present invention include inorganic or organic fillers such as silica, calcium carbonate, kaolin, calcined kaolin, diatomite, talc, titanium oxide, aluminum hydroxide and the like.

<Lubricant>

Examples of the lubricant to be used in the present invention include metal salt of fatty acid such as zinc stearate and calcium stearate, waxes, silicone resins and the like.

<Other Auxiliary Agent>

In the present invention, various auxiliary agents such as dispersing agent, antifoaming agent, and fluorescence dye can be used as long as they do not inhibit the desired effect on the above-mentioned problems.

While the amounts of the leuco dye, developer, sensitizer and various other components to be used in the thermal recording layer of the present invention are determined according to the desired property and recording properties and are not particularly limited, 0.5-10 parts by weight of a developer, about 0.5-10 parts by weight of a sensitizer, and 0.01-10 parts by weight of other components are generally used per 1 part by weight of the leuco dye.

<Support>

Support is not subject to any particular limitation with regard to its shape, structure, size, material and the like, and can be appropriately selected according to the object. Examples of the shape include sheet, roll, flat plate and the like. The structure may be a single layer structure or a laminate structure, and the size can be appropriately selected according to the use of the object thermal recording material and the like. Examples of the material include plastic film, synthetic paper, wood free paper, waste paper pulp, recycled paper, luster paper, oil proof paper, coated paper, art paper, cast coated paper, weak coated paper, resin laminated paper, release paper and the like. Alternatively, a composite sheet made of a combination thereof may be used as a support.

The thickness of the support is not particularly limited, and can be appropriately selected according to the object. It is preferably 30-2,000 μm, more preferably 50-1,000 μm.

In the thermal recording material of the present invention, a method of forming a thermal recording layer is not particularly limited, and a generally-known method can be used for the formation. For example, a leuco dye, a developer, a sensitizer, and a material to be added as necessary are divided into fine particles having a particle size of several microns or below by a grinding machine or appropriate emulsifying apparatus such as ball mill, attritor and sand grinder and a binder and various addition materials are added according to the object to give a coating solution. As a solvent to be used for this coating solution, water, alcohol and the like can be used, and a solid content thereof is generally about 20-40 wt %.

The thermal recording material of the present invention can be obtained by applying the above-mentioned coating solution on at least one surface of a support to form a thermal recording layer. The method of coating is not particularly limited and the coating can be performed according to a well-known conventional technique. For example, an off-machine coater and an on-machine coater provided with various coaters such as air knife coater, rod blade coater, bent blade coater, beveled-blade coater, roll coater and curtain coater are appropriately selected and used.

The amount of the thermal recording layer to be coated can be appropriately determined according to its composition, use of the thermal recording material and the like. It is generally 1-20 g/m$^2$, preferably 2-12 g/m$^2$ in dry weight.

<Protection Layer>

In the thermal recording material of the present invention, a protection layer can be formed on the thermal recording layer. Generally, when the storability (heat resistance, plasticizer resistance etc.) of blank area and images in the recorded area are improved by forming a protection layer on the thermal recording layer, color-developing sensitivity at low energy application (i.e., start-up sensitivity) becomes particularly inferior to that without the protection layer, since the application energy decreases in the protection layer. However, with the thermal recording material of the present invention, the start-up sensitivity is fine even when a protection layer is formed on the thermal recording layer.

The kind and amount of various components to be used for the protection layer can be determined according to the desired property and recording properties, and is not particularly limited.

In the thermal recording material of the present invention, an under layer of a polymer substance containing a pigment and the like can also be formed between the support and the thermal recording layer, to further increase the color-developing sensitivity. It is also possible to provide a back layer on the face opposite to the thermal recording layer of the support to achieve curl corrections. An intermediate layer (heat insulating layer) may also be formed between the support and the under layer, between the thermal recording layer and the protective layer, and between the support and the back layer. In addition, various known techniques in the field of thermal recording materials can be appropriately added as necessary, such as a smoothing treatment by supercalender etc. after forming each layer by coating.

EXAMPLES

The present invention is explained in detail in the following by referring to Examples, which are not to be construed as limitative.

Synthetic Example 1

Synthesis of Exemplary Compound (a3)

4-Acetoxybenzenesulfonyl chloride (84 g), 2,6-dimethylphenol (36 g) and toluene (400 ml) were placed in a 1000 ml four-necked flask, triethylamine (45 g) was added dropwise with stirring, and the mixture was reacted at 25° C. for 3 hr. After completion of the reaction, 10% aqueous acetic acid solution was added to the reaction mixture, and an extraction operation was performed. The organic layer was washed several times with water until pH was near neutral pH, and toluene was evaporated under reduced pressure from the organic layer. Methanol (100 ml) and potassium carbonate (16 g) were added to the residue, and the mixture was stirred under reflux for 1 hr, and subjected to a deacetylation reaction. After completion of the reaction, 10% aqueous acetic acid solution was added to the reaction mixture, and the mixture was extracted with ethyl acetate. After washing with water and drying (over anhydrous sodium sulfate), ethyl acetate was evaporated, and the residue was purified by a recrystallization method to give the object exemplary compound (a3) (purity 98%, HPLC analysis results) as white crystals.

The conditions of the analysis by high performance liquid chromatography (HPLC analysis) are as follows.

column: CAPCELL PAK C18 manufactured by SHISEIDO particle size: 3 μm inner diameter×length: inner diameter 4.6 mm×length 75 mm eluent: acetonitrile: 0.05 vol % aqueous phosphoric acid solution=60:40 (volume ratio)

flow rate: 0.8 ml/min wavelength: 254 nm injection volume: 1 μL column temperature: 40° C.

analysis time: 15 min sample concentration: about 10 ppm

The properties of the obtained white crystals were as follows.

<Melting Point>

149° C.

The melting point is the value measured according to JIS K 0064.

<IR Spectrum (ATR)>

3432, 1601, 1588, 1473, 1437, 1437, 1347, 1284, 1218, 1080, 873, 757, 681, 537 cm$^{-1}$

<$^1$H-NMR Spectrum (270 MHz, CDCl$_3$)>

δ2.11 (6H, s), 5.76 (1H, OH, brd), 6.96 (2H, d, J=15.9 Hz), 7.02-7.09 (3H, m), 7.85 (2H, d, J=15.9 Hz)

<Molecular Weight>

276.8 (M−1)

Synthetic Example 2

Synthesis of Exemplary Compound (a4)

4-Acetoxybenzenesulfonyl chloride (18.3 g), 2,4,6-trimethylphenol (8.85 g) and toluene (100 ml) were placed in a 300 ml four-necked flask, triethylamine (9.87 g) was added dropwise with stirring, and the mixture was reacted at 25° C. for 3 hr. After completion of the reaction, 10% aqueous acetic acid solution was added to the reaction mixture, and an extraction operation was performed. The organic layer was washed several times with water until pH was near neutral pH, and toluene was evaporated under reduced pressure from the organic layer. Methanol (100 ml) and potassium carbonate (3 g) were added to the residue, and the mixture was stirred under reflux for 1 hr, and subjected to a deacetylation reaction. After completion of the reaction, 10% aqueous acetic acid solution was added to the reaction mixture, and the mixture was extracted with ethyl acetate. After washing with water and drying (over anhydrous sodium sulfate), ethyl acetate was evaporated, and the residue was purified by a recrystallization method to give the object exemplary compound (a4) (purity 99%) as white crystals.

The properties of the obtained white crystals were as follows.

<Melting Point>

123° C.

<IR Spectrum (ATR)>

3450, 3413, 2920, 1600, 1587, 1480, 1440, 1337, 1190, 1160, 1086, 845, 692, 591, 540 cm$^{-1}$

<$^1$H-NMR Spectrum (270 MHz, CDCl$_3$-d$_6$)>

δ2.08 (6H, s), 2.24 (3H, s), 6.82 (2H, s), 6.95 (2H, d, J=8.9 Hz), 7.83 (2H, d, J=8.9 Hz)

<Molecular Weight>

290.8 (M−1)

Synthetic Example 3

Synthesis of Exemplary Compound (a6)

4-Acetoxybenzenesulfonyl chloride (16.9 g), thymol(2-isopropyl-5-methylphenol) (9.01 g) and toluene (100 ml) were placed in a 300 ml four-necked flask, triethylamine (9.11 g) was added dropwise with stirring, and the mixture was reacted at 25° C. for 3 hr. After completion of the reaction, 10% aqueous acetic acid solution was added to the reaction mixture, and an extraction operation was performed. The organic layer was washed several times with water until pH was near neutral pH, and toluene was evaporated under reduced pressure from the organic layer. Methanol (100 ml) and potassium carbonate (3 g) were added to the residue, and the mixture was stirred under reflux for 1 hr, and subjected to a deacetylation reaction. After completion of the reaction, 10% aqueous acetic acid solution was added to the reaction mixture, and the mixture was extracted with ethyl acetate. After washing with water and drying (over anhydrous sodium sulfate), ethyl acetate was evaporated, and the residue was purified by a recrystallization method to give the object exemplary compound (a6) (purity 98%) as white crystals.

The properties of the obtained white crystals were as follows.

<Melting Point>

103-106° C.

<IR Spectrum (ATR)>

3372, 2968, 1586, 1499, 1447, 1348, 1285, 1181, 1155, 1075, 942, 837, 800, 721, 554 cm$^{-1}$

<$^1$H-NMR Spectrum (270 MHz, CDCl$_3$)>

δ1.01 (3H, s), 1.03 (3H, s), 2.26 (3H, s), 3.03 (1H, sept, J=6.6 Hz), 6.01 (1H, OH, brd), 6.89-6.95 (3H, m), 7.01-7.04 (1H, m), 7.11-7.15 (1H, m), 7.75 (2H, d, J=8.9 Hz)

<Molecular Weight>

304.9 (M−1)

Synthetic Example 4

Synthesis of Exemplary Compound (a8)

4-Acetoxybenzenesulfonyl chloride (18.3 g), 2-methoxy-p-cresol (8.9 g) and toluene (100 ml) were placed in a 300 ml four-necked flask, triethylamine (9.87 g) was added dropwise with stirring, and the mixture was reacted at 25° C. for 3 hr. After completion of the reaction, 10% aqueous acetic acid solution was added to the reaction mixture, and an extraction operation was performed. The organic layer was washed several times with water until pH was near neutral pH, and toluene was evaporated under reduced pressure from the organic layer. Methanol (100 ml) and potassium carbonate (3 g) were added to the residue, and the mixture was stirred under reflux for 1 hr, and subjected to a deacetylation reaction. After completion of the reaction, 10% aqueous acetic acid solution was added to the reaction mixture, and the mixture was extracted with ethyl acetate. After washing with water and drying (over anhydrous sodium sulfate), ethyl acetate was evaporated, and the residue was purified by a recrystallization method to give the object exemplary compound (a8) (purity 99%) as white crystals.

The properties of the obtained white crystals were as follows.

<Melting Point>

101° C.

<IR Spectrum (ATR)>

3396, 1600, 1588, 1503, 1470, 1347, 1287, 1193, 1178, 1144, 1112, 1088, 1030, 855, 809, 753, 704, 559, 540 cm$^{-1}$

<$^1$H-NMR Spectrum (270 MHz, CDCl$_3$)>

δ2.31 (3H, s), 3.56 (3H, s), 6.01 (1H, s), 6.64-6.69 (3H, m), 6.90 (2H, d, J=8.9Hz), 7.73 (2H, d, J=8.9Hz)

<Molecular Weight>

292.8 (M−1)

In the following Examples and Comparative Examples, an under layer and a thermal recording layer were formed on one surface of a support.

A coating solution used for each coating layer of a thermal recording medium was prepared as follows. In the explanation, parts and % mean parts by weight and wt %, respectively.

Under Layer Coating Solution

| | |
|---|---|
| calcined kaolin (manufactured by BASF, trade name: ANSILEX 90) | 90.0 parts |
| styrene-butadiene copolymer latex (solid content 50%) | 10.0 parts |
| water | 50.0 parts |

A mixture of the above-mentioned composition was mixed with stirring to prepare an under layer coating solution.

Thermal Recording Layer Coating Solution

The following solutions A-E were separately subjected to wet grinding by a sand grinder until the average particle size of the solid material in the liquid became about 0.5 μm. The average particle size here is a volume average diameter in volume standard distribution, and was measured by a laser diffraction/scattering particle size distribution analyzer.

| solution A (developer dispersion) | |
|---|---|
| 2,6 dimethylphenyl 4'-hydroxybenzenesulfonate (exemplary compound a3) | 6.0 parts |
| 10% aqueous polyvinyl alcohol solution | 5.0 parts |
| water | 1.5 parts |
| solution B (second developer dispersion) | |
| bis(3-allyl-4-hydroxyphenyl)sulfone (second developer) | 6.0 parts |
| 10% aqueous polyvinyl alcohol solution | 5.0 parts |
| water | 1.5 parts |
| solution C (leuco dye dispersion) | |
| 3-dibutylamino-6-methyl-7-anilinofluorane (manufactured by YAMAMOTO CHEMICALS INC., trade name: ODB-2) | 6.0 parts |
| 10% aqueous polyvinyl alcohol solution | 5.0 parts |
| water | 1.5 parts |
| solution D (sensitizer dispersion) | |
| 1,2-di-(3-methylphenoxy)ethane (manufactured by SANKO CO., LTD., trade name: KS-232) | 6.0 parts |
| 10% aqueous polyvinyl alcohol solution | 5.0 parts |
| water | 1.5 parts |
| solution E (hindered phenol compound dispersion) | |
| 1,1,3-tris(2-methyl-4-hydroxy-5-t-butylphenyl)butane (manufactured by OSAKA SHINYAKU CO., LTD., trade name: OS-930) | 6.0 parts |
| 10% aqueous polyvinyl alcohol solution | 5.0 parts |
| water | 1.5 parts |

Then, respective dispersions were mixed at the following proportion to give thermal recording layer coating solution 1.

| | |
|---|---|
| solution A (developer dispersion) | 36.0 parts |
| solution C (leuco dye dispersion) | 18.0 parts |
| Silica (manufactured by MIZUSAWA INDUSTRIAL CHEMICALS, LTD., trade name: P537 25% dispersion) | 17.5 parts |
| 10% aqueous polyvinyl alcohol solution | 25.0 parts |

Example 1

An under layer coating solution was applied to one surface of wood free paper (substrate paper, basis weight 47 g/m$^2$) with a Mayer bar such that the coating amount was 10.0 g/m$^2$ in a dry weight and dried (forced air dryer, 60° C., 2 min) to give undercoated paper. The thermal recording layer coating solution 1 was applied to an under layer of the undercoated paper such that the coating amount was 3.5 g/m$^2$ in a dry weight and dried (forced air dryer, 60° C., 2 min). The obtained sheet was subjected to a supercalender treatment to achieve a smoothness degree of 500-1000 sec to give a thermal recording material.

Example 2

In the same manner as in Example 1 except that the exemplary compound (a3) in solution A (developer dispersion) of Example 1 was changed to exemplary compound (a4), a thermal recording material was prepared.

Example 3

In the same manner as in Example 1 except that the exemplary compound (a3) in solution A (developer dispersion) of Example 1 was changed to exemplary compound (a8), a thermal recording material was prepared.

Example 4

In the same manner as in Example 1 except that the exemplary compound (a3) in solution A (developer dispersion) of Example 1 was changed to exemplary compound (a6), a thermal recording material was prepared.

Comparative Example 1

In the same manner as in Example 1 except that the exemplary compound (a3) in solution A (developer dispersion) of Example 1 was changed to 4-t-butylphenyl 4'-hydroxybenzenesulfonate, a thermal recording material was prepared.

Comparative Example 2

In the same manner as in Example 1 except that the exemplary compound (a3) in solution A (developer dispersion) of Example 1 was changed to 4-chlorophenyl 4'-hydroxybenzenesulfonate, a thermal recording material was prepared.

Comparative Example 3

In the same manner as in Example 1 except that the exemplary compound (a3) in solution A (developer dispersion) of Example 1 was changed to bisphenol S (4,4'-dihydroxydiphenylsulfone), a thermal recording material was prepared.

Comparative Example 4

In the same manner as in Example 1 except that the exemplary compound (a3) in solution A (developer dispersion) of Example 1 was changed to bisphenol A (4,4'-isopropylidenediphenol), a thermal recording material was prepared.

Comparative Example 5

In the same manner as in Example 1 except that the exemplary compound (a3) in solution A (developer dispersion) of Example 1 was changed to 4-hydroxy-4'-allyloxydiphenylsulfone obtained in the method described in JP-B-2500532, a thermal recording material was prepared.

Comparative Example 6

In the same manner as in Example 1 except that the exemplary compound (a3) in solution A (developer dispersion) of Example 1 was changed to 4-hydroxy-4'-isopropoxydiphenylsulfone (manufactured by Nippon Soda Co., Ltd., trade name: D-8), a thermal recording material was prepared.

Then, respective dispersions were mixed at the following proportion to give thermal recording layer coating solution 2.

| | |
|---|---|
| solution A (developer dispersion) | 36.0 parts |
| solution C (leuco dye dispersion) | 18.0 parts |
| solution D (sensitizer dispersion) | 36.0 parts |
| silica (manufactured by MIZUSAWA INDUSTRIAL CHEMICALS, LTD., trade name: P537 25% dispersion) | 17.5 parts |
| 10% aqueous polyvinyl alcohol solution | 25.0 parts |

Example 5

An under layer coating solution was applied to one surface of wood free paper (substrate paper, basis weight 47 g/m$^2$) by a Mayer bar such that the coating amount was 10.0 g/m$^2$ in a dry weight and dried (forced air dryer, 60° C., 2 min) to give undercoated paper. The thermal recording layer coating solution 2 was applied to an under layer of the undercoated paper such that the coating amount was 3.5 g/m$^2$ in a dry weight and dried (forced air dryer, 60° C., 2 min). The obtained sheet was subjected to a supercalender treatment to achieve a smoothness degree of 500-1000 sec to give a thermal recording material.

Example 6

In the same manner as in Example 5 except that 1,2-di-(3-methylphenoxy)ethane in solution D (sensitizer dispersion) of Example 5 was changed to p-benzyloxynaphthalene, a thermal recording material was prepared.

Example 7

In the same manner as in Example 5 except that 1,2-di-(3-methylphenoxy)ethane in solution D (sensitizer dispersion) of Example 5 was changed to diphenylsulfone, a thermal recording material was prepared.

Example 8

In the same manner as in Example 5 except that 1,2-di-(3-methylphenoxy)ethane in solution D (sensitizer dispersion) of Example 5 was changed to stearic acid amide, a thermal recording material was prepared.

Comparative Example 7

In the same manner as in Example 5 except that the exemplary compound (a3) in solution A (developer dispersion) of Example 5 was changed to 4-hydroxy-4'-isopropoxydiphenylsulfone (manufactured by Nippon Soda Co., Ltd., trade name: D-8), a thermal recording material was prepared.

Comparative Example 8

In the same manner as in Example 6 except that the exemplary compound (a3) in solution A (developer dispersion) of Example 6 was changed to 4-hydroxy-4'-isopropoxydiphenylsulfone (manufactured by Nippon Soda Co., Ltd., trade name: D-8), a thermal recording material was prepared.

Comparative Example 9

In the same manner as in Example 7 except that the exemplary compound (a3) in solution A (developer dispersion) of Example 7 was changed to 4-hydroxy-4'-isopropoxydiphenylsulfone (manufactured by Nippon Soda Co., Ltd., trade name: D-8), a thermal recording material was prepared.

Comparative Example 10

In the same manner as in Example 8 except that the exemplary compound (a3) in solution A (developer dispersion) of Example 8 was changed to 4-hydroxy-4'-isopropoxydiphenylsulfone (manufactured by Nippon Soda Co., Ltd., trade name: D-8), a thermal recording material was prepared.

Comparative Example 11

In the same manner as in Example 5 except that the exemplary compound (a3) in solution A (developer dispersion) of Example 5 was changed to 4-hydroxy-4'-allyloxydiphenylsulfone obtained in the method described in JP-B-2500532, a thermal recording material was prepared.

Comparative Example 12

In the same manner as in Example 5 except that the exemplary compound (a3) in solution A (developer dispersion) of Example 5 was changed to bisphenol A (4,4'-isopropylidenediphenol), a thermal recording material was prepared.

Then, respective dispersions were mixed at the following proportion to give thermal recording layer coating solution 3.

| | |
|---|---|
| solution A (developer dispersion) | 25.2 parts |
| solution B (second developer dispersion) | 10.8 parts |
| solution C (leuco dye dispersion) | 18.0 parts |
| solution D (sensitizer dispersion) | 36.0 parts |
| silica (manufactured by MIZUSAWA INDUSTRIAL CHEMICALS, LTD., trade name: P537 25% dispersion) | 17.5 parts |
| 10% aqueous polyvinyl alcohol solution | 25.0 parts |

Example 9

An under layer coating solution was applied to one surface of wood free paper (substrate paper, basis weight 47 g/m$^2$) by a Mayer bar such that the coating amount was 10.0 g/m$^2$ in a dry weight and dried (forced air dryer, 60° C., 2 min) to give undercoated paper. The thermal recording layer coating solution 3 was applied to an under layer of the undercoated paper such that the coating amount was 3.5 g/m$^2$ in a dry weight and dried (forced air dryer, 60° C., 2 min). The obtained sheet was subjected to a supercalender treatment to achieve a smoothness degree of 500-1000 sec to give a thermal recording material.

Example 10

In the same manner as in Example 9 except that bis(3-allyl-4-hydroxyphenyl)sulfone in solution B (second developer dispersion) of Example 9 was changed to 4-hydroxy-4'-allyloxydiphenylsulfone obtained in the method described in JP-B-2500532, a thermal recording material was prepared.

Example 11

In the same manner as in Example 9 except that bis(3-allyl-4-hydroxyphenyl)sulfone in solution B (second developer dispersion) of Example 9 was changed to 4-hydroxy-4'-propoxydiphenylsulfone (manufactured by API Corporation, trade name: TOMILAC KN), a thermal recording material was prepared.

Example 12

In the same manner as in Example 9 except that bis(3-allyl-4-hydroxyphenyl)sulfone in solution B (second developer dispersion) of Example 9 was changed to bisphenol S (4,4'-dihydroxydiphenylsulfone), a thermal recording material was prepared.

Example 13

In the same manner as in Example 9 except that bis(3-allyl-4-hydroxyphenyl)sulfone in solution B (second developer dispersion) of Example 9 was changed to bisphenol C (2,2'-bis(4-hydroxy-3-methylphenyl)propane), a thermal recording material was prepared.

Example 14

In the same manner as in Example 9 except that bis(3-allyl-4-hydroxyphenyl)sulfone in solution B (second developer dispersion) of Example 9 was changed to bisphenol A (4,4'-isopropylidenediphenol), a thermal recording material was prepared.

Example 15

In the same manner as in Example 9 except that bis(3-allyl-4-hydroxyphenyl)sulfone in solution B (second developer dispersion) of Example 9 was changed to phenol-formalin condensation products described in WO02/098674 (manufactured by API Corporation, trade name: TOMILAC 224), a thermal recording material was prepared.

Example 16

In the same manner as in Example 9 except that the amount of solution A (developer dispersion) of Example 9 was changed to 36.0 parts, and bis(3-allyl-4-hydroxyphenyl)sulfone in solution B (second developer dispersion) was changed to a diphenylsulfone compound described in JP-B-4004289 (manufactured by API Corporation, trade name: TOMILAC 214), a thermal recording material was prepared.

Example 17

In the same manner as in Example 9 except that the amount of solution A (developer dispersion) of Example 9 was changed to 32.4 parts, bis(3-allyl-4-hydroxyphenyl)sulfone in solution B (second developer dispersion) was changed to a diphenylsulfone compound described in JP-B-4004289 (manufactured by API Corporation, trade name: TOMILAC 214), and the amount of solution B (second developer dispersion) was changed to 3.6 parts, a thermal recording material was prepared.

Example 18

In the same manner as in Example 9 except that bis(3-allyl-4-hydroxyphenyl)sulfone in solution B (second developer dispersion) of Example 9 was changed to a diphenylsulfone compound described in JP-B-4004289 (manufactured by API Corporation, trade name: TOMILAC 214), a thermal recording material was prepared.

Example 19

In the same manner as in Example 9 except that the amount of solution A (developer dispersion) of Example 9 was changed to 36.0 parts, and bis(3-allyl-4-hydroxyphenyl)sulfone in solution B (second developer dispersion) was changed to a diphenylsulfone crosslinking type compound described in JP-B-3913820 (manufactured by Nippon Soda Co., Ltd., trade name: D-90), a thermal recording material was prepared.

Example 20

In the same manner as in Example 9 except that the amount of solution A (developer dispersion) of Example 9 was changed to 32.4 parts, bis(3-allyl-4-hydroxyphenyl)sulfone in solution B (second developer dispersion) was changed to a diphenylsulfone crosslinking type compound described in JP-B-3913820 (manufactured by Nippon Soda Co., Ltd., trade name: D-90), and the amount of solution B (second developer dispersion) was changed to 3.6 parts, a thermal recording material was prepared.

Example 21

In the same manner as in Example 9 except that bis(3-allyl-4-hydroxyphenyl)sulfone in solution B (second developer dispersion) of Example 9 was changed to a diphenylsulfone crosslinking type compound described in JP-B-3913820 (manufactured by Nippon Soda Co., Ltd., trade name: D-90), a thermal recording material was prepared.

Example 22

In the same manner as in Example 9 except that the amount of solution A (developer dispersion) of Example 9 was changed to 36.0 parts, and bis(3-allyl-4-hydroxyphenyl)sulfone in solution B (second developer dispersion) was changed to 4,4'-bis(3-(phenoxycarbonylamino)methylphenylureido)diphenylsulfone, a thermal recording material was prepared.

Example 23

In the same manner as in Example 9 except that the amount of solution A (developer dispersion) of Example 9 was changed to 36.0 parts, and bis(3-allyl-4-hydroxyphenyl)sulfone in solution B (second developer dispersion) was changed to a N-(p-toluenesulfonyl)-N'-(3-p-toluenesulfonyl-oxy-phenyl)urea compound described in JP-B-4601174, a thermal recording material was prepared.

Then, respective dispersions were mixed at the following proportion to give thermal recording layer coating solution 4.

| | |
|---|---|
| solution A (developer dispersion) | 36.0 parts |
| solution C (leuco dye dispersion) | 18.0 parts |
| solution D (sensitizer dispersion) | 36.0 parts |
| solution E (hindered phenol compound dispersion) | 3.6 parts |
| silica (manufactured by MIZUSAWA INDUSTRIAL CHEMICALS, LTD., trade name: P537 25% dispersion) | 17.5 parts |
| 10% aqueous polyvinyl alcohol solution | 25.0 parts |

Example 24

An under layer coating solution was applied to one surface of wood free paper (substrate paper, basis weight 47 g/m$^2$) by a Mayer bar such that the coating amount was 10.0 g/m$^2$ in a dry weight and dried (forced air dryer, 60° C., 2 min) to give undercoated paper. The thermal recording layer coating solution 4 was applied to an under layer of the undercoated paper such that the coating amount was 3.5 g/m$^2$ in a dry weight and dried (forced air dryer, 60° C., 2 min). The obtained sheet was subjected to a supercalender treatment to achieve a smoothness degree of 500-1000 sec to give a thermal recording material.

Example 25

In the same manner as in Example 24 except that 1,1,3-tris(2-methyl-4-hydroxy-5-t-butylphenyl)butane (manufactured by OSAKA SHINYAKU CO., LTD., trade name: OS-930) in solution E (hindered phenol compound dispersion) of Example 24 was changed to 1,1,3-tris(2-methyl-4-hydroxy-5-cyclohexylphenyl)butane (manufactured by ADEKA CORPORATION, trade name: DH-43), a thermal recording material was prepared.

Example 26

In the same manner as in Example 24 except that 1,1,3-tris(2-methyl-4-hydroxy-5-t-butylphenyl)butane (manufactured by OSAKA SHINYAKU CO., LTD., trade name: OS-930) in solution E (hindered phenol compound dispersion) of Example 24 was changed to 4,4'-butylidenebis-(6-t-butyl-3-methylphenol) (manufactured by API Corporation, trade name: YOSHINOX BB), a thermal recording material was prepared.

Example 27

In the same manner as in Example 24 except that 1,1,3-tris (2-methyl-4-hydroxy-5-t-butylphenyl)butane (manufactured by OSAKA SHINYAKU CO., LTD., trade name: OS-930) in solution E (hindered phenol compound dispersion) of Example 24 was changed to oligomer type hindered phenol (manufactured by ELIOCHEM, trade name: WINGSTAY L), a thermal recording material was prepared.

Example 28

In the same manner as in Example 24 except that the amount of solution E (hindered phenol compound dispersion) of Example 24 was changed to 1.8 parts, a thermal recording material was prepared.

Example 29

In the same manner as in Example 24 except that the amount of solution A (developer dispersion) of Example 24 was changed to 34.2 parts, and the amount of solution E (hindered phenol compound dispersion) was changed to 1.8 parts, a thermal recording material was prepared.

Example 30

In the same manner as in Example 24 except that the amount of solution A (developer dispersion) of Example 24 was changed to 32.4 parts, a thermal recording material was prepared.

Example 31

In the same manner as in Example 24 except that the amount of solution A (developer dispersion) of Example 24 was changed to 25.2 parts, and the amount of solution E (hindered phenol compound dispersion) was changed to 10.8 parts, a thermal recording material was prepared.

The thermal recording materials obtained in the above-mentioned Examples and Comparative Examples were evaluated as follows.

<Print Density>

Using a thermal printer (TH-PMD) manufactured by OHKURA ELECTRIC CO., LTD, checkered patterns were printed on a thermal recording material at an application energy of 0.35 mJ/dot, and the density of the blank area and images in the recorded area was measured by a Macbeth densitometer (manufactured by Gretag Macbeth, RD-914, using amber filter).

<Heat Resistance>

Using a thermal printer (TH-PMD) manufactured by OHKURA ELECTRIC CO., LTD, a test including printing checkered patterns on a thermal recording material at an application energy of 0.35 mJ/dot, and leaving the material at 60° C. for 24 hr was performed. The density of the blank area and images in the recorded area was measured by a Macbeth densitometer (manufactured by Gretag Macbeth, RD-914, using amber filter), and the residual ratio and the contrast between the recorded area and the blank area were calculated by the following formulas. The results of the residual ratio are shown in Table 1, Table 5-1 and Table 5-2. The results of the contrast are shown in Table 1.

residual ratio (%)=(density of image in recorded area after test)/(density of image in recorded area before test)×100(%)

contrast between recorded area and blank area=(density of image in recorded area after test)−(density of blank area after test)

<Plasticizer Resistance>

Using a thermal printer (TH-PMD) manufactured by OHKURA ELECTRIC CO., LTD, a test including printing checkered patterns on a thermal recording material at an application energy of 0.35 mJ/dot, bringing DIAWRAP (manufactured by MITSUBISHI PLASTICS, INC.) into contact with the front and the back, and leaving the material at 23° C. for 2 hr was performed. The density of the images in the recorded area was measured Macbeth densitometer (manufactured by Gretag Macbeth, RD-914, using amber filter), and the residual ratio was calculated by the following formula. The results are shown in Table 2, Table 5-1 and Table 5-2.

residual ratio (%)=(density of image in recorded area after test)/(density of image in recorded area before test)×100(%)

<Start-Up Sensitivity>

Using a thermal printer (TH-PMD) manufactured by OHKURA ELECTRIC CO., LTD, checkered patterns were printed on a thermal recording material at an application energy of 0.255 mJ/dot, and the density of the blank area and images in the recorded area was measured by a Macbeth densitometer (manufactured by Gretag Macbeth, RD-914, using amber filter). The results are shown in Table 3 and Table 4.

<Moisture Resistance>

Using a thermal printer (TH-PMD) manufactured by OHKURA ELECTRIC CO., LTD, checkered patterns were printed on a thermal recording material at an application energy of 0.35 mJ/dot, and the material was left standing for 24 hr in an environment of 40° C. and 90% Rh. The density of the images in the recorded area was measured by a Macbeth densitometer (manufactured by Gretag Macbeth, RD-914, using amber filter), and the residual ratio was calculated by the following formula. The results are shown in Table 5-1 and Table 5-2.

residual ratio (%)=(density of image in recorded area after test)/(density of image in recorded area before test)×100(%)

<Water Resistance>

Using a thermal printer (TH-PMD) manufactured by OHKURA ELECTRIC CO., LTD, checkered patterns were printed on a thermal recording material at an application energy of 0.35 mJ/dot, and the material was left standing for 24 hr in water at 20° C. The density of the images in the recorded area was measured by a Macbeth densitometer (manufactured by Gretag Macbeth, RD-914, using amber filter), and the residual ratio was calculated by the following formula. The results are shown in Table 5-1 and Table 5-2.

residual ratio (%)=(density of image in recorded area after test)/(density of image in recorded area before test)×100(%)

Example 32

In the same manner as in Example 24 except that 1,1,3-tris (2-methyl-4-hydroxy-5-t-butylphenyl)butane (manufactured by OSAKA SHINYAKU CO., LTD., trade name: OS-930) in solution E (hindered phenol compound dispersion) of Example 24 was changed to 2,2'-methylenebis-(4-methyl-6-t-butylphenol) (manufactured by API Corporation, trade name: YOSHINOX 425), a thermal recording material was prepared.

Example 33

In the same manner as in Example 24 except that 1,1,3-tris(2-methyl-4-hydroxy-5-t-butylphenyl)butane (manufactured by OSAKA SHINYAKU CO., LTD., trade name: OS-930) in solution E (hindered phenol compound dispersion) of Example 24 was changed to 4,4'-thiobis-(6-t-butyl-3-methylphenol) (manufactured by SUMITOMO CHEMICAL CO., LTD., trade name: SUMILIZER WXR), a thermal recording material was prepared.

The thermal recording materials obtained in the above-mentioned Examples 5 and 24-33, and Comparative Examples 1-3 were evaluated as follows.

<Print Density>

Using a thermal printer (TH-PMD) manufactured by OHKURA ELECTRIC CO., LTD, checkered patterns were printed on a thermal recording material at an application energy of 0.35 mJ/dot, and the density of the blank area and images in the recorded area was measured by a Macbeth densitometer (manufactured by Gretag Macbeth, RD-914, using amber filter).

<Heat Resistance>

Using a thermal printer (TH-PMD) manufactured by OHKURA ELECTRIC CO., LTD, a test including printing checkered patterns on a thermal recording material at an application energy of 0.35 mJ/dot, and leaving the material at 60° C. for 24 hr was performed. The density of the blank area and images in the recorded area was measured by a Macbeth densitometer (manufactured by Gretag Macbeth, RD-914, using amber filter), and the residual ratio and the contrast between the recorded area and the blank area were calculated by the following formulas. The results are shown in Table 6.

residual ratio (%)=(density of image in recorded area after test)/(density of image in recorded area before test)×100(%)

contrast between recorded area and blank area=(density of image in recorded area after test)−(density of blank area after test)

TABLE 1 evaluation results of heat resistance (no sensitizer)

| | before test | | heat resistance | | | |
|---|---|---|---|---|---|---|
| | blank area | recorded area | blank area | recorded area | residual ratio (%) | contrast |
| Example 1 | 0.07 | 1.35 | 0.17 | 1.19 | 88% | 1.02 |
| Example 2 | 0.11 | 1.31 | 0.33 | 1.25 | 95% | 0.92 |
| Comparative Example 1 | 0.13 | 1.30 | 0.92 | 1.13 | 87% | 0.21 |
| Comparative Example 2 | 0.23 | 1.26 | 1.11 | 1.27 | 101% | 0.16 |
| Comparative Example 3 | 0.08 | 0.50 | 0.10 | 0.53 | 106% | 0.43 |

TABLE 2 evaluation results of plasticizer resistance (no sensitizer)

| | plasticizer resistance | | |
|---|---|---|---|
| | recorded area | | residual ratio |
| | before test | after test | (%) |
| Example 1 | 1.35 | 1.11 | 82% |
| Example 2 | 1.31 | 0.96 | 73% |
| Example 3 | 1.30 | 1.07 | 82% |
| Example 4 | 1.22 | 0.96 | 79% |
| Comparative Example 1 | 1.30 | 0.71 | 55% |
| Comparative Example 2 | 1.26 | 0.85 | 67% |
| Comparative Example 3 | 0.50 | 0.41 | 82% |
| Comparative Example 4 | 1.30 | 0.25 | 19% |
| Comparative Example 5 | 1.13 | 0.32 | 28% |

TABLE 3 evaluation results of start-up sensitivity (no sensitizer)

| | | recorded area (application energy) | |
|---|---|---|---|
| | blank area | start-up sensitivity 0.255 mJ/dot | print density 0.35 mJ/dot |
| Example 1 | 0.07 | 0.98 | 1.35 |
| Example 2 | 0.11 | 1.04 | 1.31 |
| Example 3 | 0.10 | 1.03 | 1.30 |
| Example 4 | 0.11 | 0.99 | 1.22 |
| Comparative Example 3 | 0.08 | 0.13 | 0.50 |
| Comparative Example 4 | 0.07 | 0.57 | 1.30 |
| Comparative Example 5 | 0.06 | 0.43 | 1.13 |
| Comparative Example 6 | 0.07 | 0.65 | 1.22 |

TABLE 4 evaluation results of start-up sensitivity (with sensitizer)

| | | recorded area (application energy) | |
|---|---|---|---|
| | blank area | start-up sensitivity 0.255 mJ/dot | print density 0.35 mJ/dot |
| Example 5 | 0.07 | 1.35 | 1.40 |
| Example 6 | 0.06 | 1.24 | 1.27 |
| Example 7 | 0.08 | 1.19 | 1.29 |
| Example 8 | 0.07 | 1.08 | 1.25 |
| Example 9 | 0.07 | 1.35 | 1.40 |
| Example 10 | 0.07 | 1.35 | 1.40 |
| Example 11 | 0.07 | 1.33 | 1.39 |
| Example 12 | 0.08 | 1.30 | 1.38 |
| Example 13 | 0.07 | 1.31 | 1.36 |
| Example 14 | 0.07 | 1.34 | 1.38 |
| Example 15 | 0.06 | 1.33 | 1.38 |
| Example 16 | 0.07 | 1.33 | 1.39 |
| Example 17 | 0.07 | 1.32 | 1.36 |
| Example 18 | 0.08 | 1.26 | 1.32 |
| Example 19 | 0.07 | 1.33 | 1.39 |
| Example 20 | 0.08 | 1.32 | 1.37 |
| Example 21 | 0.07 | 1.25 | 1.32 |
| Example 22 | 0.07 | 1.26 | 1.30 |
| Example 23 | 0.07 | 1.25 | 1.33 |
| Example 24 | 0.07 | 1.29 | 1.40 |
| Example 25 | 0.07 | 1.31 | 1.37 |
| Example 26 | 0.07 | 1.35 | 1.40 |
| Example 27 | 0.06 | 1.36 | 1.40 |
| Example 28 | 0.07 | 1.31 | 1.38 |
| Example 29 | 0.06 | 1.32 | 1.37 |
| Example 30 | 0.06 | 1.30 | 1.36 |

TABLE 4-continued evaluation results of start-up sensitivity (with sensitizer)

| | blank area | recorded area (application energy) | |
|---|---|---|---|
| | | start-up sensitivity 0.255 mJ/dot | print density 0.35 mJ/dot |
| Example 31 | 0.07 | 1.27 | 1.33 |
| Comparative Example 7 | 0.07 | 1.22 | 1.30 |
| Comparative Example 8 | 0.06 | 1.16 | 1.22 |
| Comparative Example 9 | 0.06 | 1.01 | 1.21 |
| Comparative Example 10 | 0.06 | 0.89 | 1.18 |
| Comparative Example 11 | 0.06 | 1.06 | 1.30 |
| Comparative Example 12 | 0.07 | 1.22 | 1.33 |

TABLE 5-1 evaluation results of heat resistance, plasticizer resistance, moisture resistance and water resistance (with sensitizer)

| | before test | | heat resistance | plasticizer resistance | moisture resistance | water resistance |
|---|---|---|---|---|---|---|
| | blank area | recorded area | recorded area residual ratio (%) | recorded area residual ratio (%) | recorded area residual ratio (%) | recorded area residual ratio (%) |
| Example 5 | 0.07 | 1.40 | 85% | 74% | 93% | 56% |
| Example 6 | 0.06 | 1.27 | 87% | 84% | 93% | 47% |
| Example 7 | 0.08 | 1.29 | 86% | 80% | 92% | 63% |
| Example 8 | 0.07 | 1.25 | 82% | 80% | 89% | 60% |
| Example 9 | 0.07 | 1.40 | 91% | 83% | 97% | 78% |
| Example 10 | 0.07 | 1.40 | 89% | 87% | 96% | 66% |
| Example 11 | 0.07 | 1.39 | 89% | 80% | 95% | 65% |
| Example 12 | 0.08 | 1.38 | 92% | 82% | 96% | 68% |
| Example 13 | 0.07 | 1.36 | 87% | 78% | 95% | 77% |
| Example 14 | 0.07 | 1.38 | 87% | 71% | 93% | 63% |
| Example 15 | 0.06 | 1.38 | 88% | 66% | 94% | 80% |
| Example 16 | 0.07 | 1.39 | 91% | 87% | 96% | 68% |
| Example 17 | 0.07 | 1.36 | 91% | 77% | 96% | 68% |
| Example 18 | 0.08 | 1.32 | 91% | 78% | 95% | 78% |
| Example 19 | 0.07 | 1.39 | 92% | 88% | 97% | 74% |
| Example 20 | 0.08 | 1.37 | 92% | 80% | 96% | 68% |

TABLE 5-2 evaluation results of heat resistance, plasticizer resistance, moisture resistance and water resistance (with sensitizer)

| | before test | | heat resistance | plasticizer resistance | moisture resistance | water resistance |
|---|---|---|---|---|---|---|
| | blank area | recorded area | recorded area residual ratio (%) | recorded area residual ratio (%) | recorded area residual ratio (%) | recorded area residual ratio (%) |
| Example 21 | 0.07 | 1.32 | 93% | 79% | 96% | 80% |
| Example 22 | 0.07 | 1.30 | 90% | 81% | 94% | 75% |
| Example 23 | 0.07 | 1.33 | 93% | 90% | 96% | 64% |
| Example 24 | 0.07 | 1.40 | 88% | 83% | 94% | 72% |
| Example 25 | 0.07 | 1.37 | 88% | 77% | 95% | 75% |
| Example 26 | 0.07 | 1.40 | 87% | 74% | 91% | 71% |
| Example 27 | 0.06 | 1.40 | 89% | 79% | 94% | 65% |
| Example 28 | 0.07 | 1.38 | 87% | 84% | 94% | 65% |
| Example 29 | 0.06 | 1.37 | 88% | 74% | 93% | 64% |
| Example 30 | 0.06 | 1.36 | 89% | 70% | 95% | 79% |
| Example 31 | 0.07 | 1.33 | 93% | 62% | 97% | 93% |

TABLE 6 evaluation results of heat resistance

| | before test | | after test | | |
|---|---|---|---|---|---|
| | blank area | recorded area | blank area | recorded area | contrast |
| Example 5 | 0.07 | 1.40 | 0.22 | 1.19 | 0.97 |
| Example 24 | 0.07 | 1.40 | 0.16 | 1.23 | 1.07 |
| Example 25 | 0.07 | 1.37 | 0.16 | 1.20 | 1.04 |
| Example 26 | 0.07 | 1.40 | 0.19 | 1.22 | 1.03 |
| Example 27 | 0.06 | 1.40 | 0.20 | 1.24 | 1.04 |
| Example 28 | 0.07 | 1.38 | 0.17 | 1.21 | 1.04 |
| Example 29 | 0.06 | 1.37 | 0.15 | 1.21 | 1.06 |
| Example 30 | 0.06 | 1.36 | 0.15 | 1.23 | 1.08 |
| Example 31 | 0.07 | 1.33 | 0.14 | 1.26 | 1.12 |
| Example 32 | 0.07 | 1.37 | 0.22 | 1.16 | 0.94 |
| Example 33 | 0.07 | 1.39 | 0.23 | 1.21 | 0.98 |
| Comparative Example 1 | 0.13 | 1.30 | 0.92 | 1.13 | 0.21 |
| Comparative Example 2 | 0.23 | 1.26 | 1.11 | 1.27 | 0.16 |
| Comparative Example 3 | 0.08 | 0.50 | 0.10 | 0.53 | 0.43 |

As is clear from the results of Table 1, Examples 1 and 2 using the phenolsulfonic acid aryl ester of the present invention as a developer showed sufficiently high color-developing sensitivity and clear contrast between the blank area and the recorded area after the heat resistance test, as compared to Comparative Examples 1-3 using conventional developers.

In addition, as is clear from the results of Table 2, Examples 1-4 using the phenolsulfonic acid aryl ester of the present invention as a developer also showed superior plasticizer resistance as compared to Comparative Examples 1-5 using conventional developers.

Furthermore, even when sensitizer was not added, Examples 1-4 showed high color-developing sensitivity at a low application energy (0.255 mJ/dot) and were superior in start-up sensitivity (Table 3).

When various sensitizers were added, Examples 5-8 using the phenolsulfonic acid aryl ester of the present invention as a developer showed high color-developing sensitivity even at a low application energy (0.255 mJ/dot), and were superior in start-up sensitivity, as compared to Comparative Examples 7-12 using conventional developers. Even Examples 9-31 using the second developer and hindered phenol compounds in combination showed sufficiently high color-developing sensitivity (Table 4).

In addition, as is clear from the results of Table 5-1 and Table 5-2, Examples 5-8 using the phenolsulfonic acid aryl ester of the present invention as a developer showed sufficient color-developing sensitivity and particularly good recorded area residual ratios in the plasticizer resistance evaluation and moisture resistance evaluation. Examples 9-23 using the second developer in combination showed further improved recorded area residual ratios in the heat resistance evaluation, water resistance evaluation and moisture resistance evaluation, while sufficiently maintaining color-developing sensitivity. Examples 24-31 using hindered phenol compounds in combination showed further improved recorded area residual ratios in the water resistance evaluation and moisture resistance evaluation, while sufficiently maintaining color-developing sensitivity.

Furthermore, as is clear from the results of Table 6, Examples 24-31 using a particular hindered phenol compound showed further improved heat resistance of the blank area.

Therefore, the phenolsulfonic acid aryl ester of the present invention is an extremely superior developer which shows extremely high color-developing sensitivity, provides good image density even when printed at a low application energy (i.e., high start-up sensitivity), and shows good storability (heat resistance, plasticizer resistance etc.) of blank area and images in the recorded area.

The present invention is based on a patent application No. 2010-208341 filed in Japan, the contents of which are incorporated in full herein.

The invention claimed is:

1. A phenolsulfonic acid aryl ester represented by the following formula:

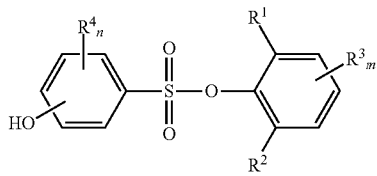

wherein
$R^1$ and $R^2$ are each independently an alkyl group having 1 to 8 carbon atoms;
$R^3$ is an alkyl group having 1 to 8 carbon atoms;
$R^4$ is an alkyl group having 1 to 8 carbon atoms, an alkenyl group having 2 to 8 carbon atoms, an alkoxy group having 1 to 8 carbon atoms, a cyano group, an aryl group having 6 to 14 carbon atoms or an aralkyl group having 7 to 15 carbon atoms;
m is an integer of 0-3;
and n is an integer of 0-4.

2. A developer for a thermal recording material, comprising at least one kind of the phenolsulfonic acid aryl ester according to claim 1.

3. A thermal recording material comprising a support and a thermal recording layer comprising a colorless or pale-colored basic leuco dye and a developer for color development of the basic leuco dye, which layer is laminated on at least one surface of the support, wherein the developer contains at least one kind of phenolsulfonic acid aryl ester according to claim 1.

4. The thermal recording material according to claim 3, wherein the developer further contains at least one kind of a second developer selected from the group consisting of a bisphenol compound, a bisphenol sulfone compound, a urea compound and a novolac type phenol compound.

5. The thermal recording material according to claim 3, wherein the thermal recording layer contains at least one kind of sensitizer selected from the group consisting of 1,2-di-(3-methylphenoxy)ethane, fatty acid amide having 10 to 21 carbon atoms, β-benzyloxynaphthalene and diaphenylsulfone.

6. The thermal recording material according to claim 3, wherein the thermal recording layer contains a hindered phenol compound.

7. The thermal recording material according to claim 6, wherein the hindered phenol compound is at least one kind selected from the group consisting of a compound represented by the following formula (3), a compound represented by the following formula (5) and a compound represented by the following formula (6):

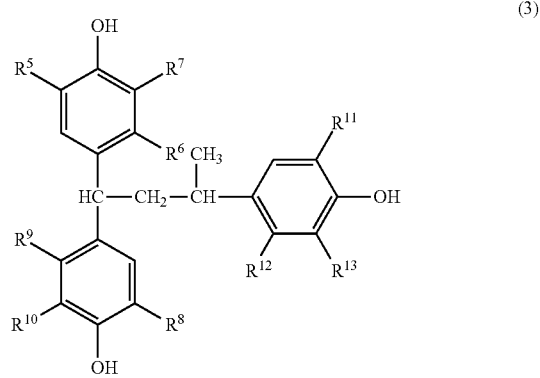

wherein $R^5$, $R^8$ and $R^{11}$ are each independently an alkyl group having 1 to 8 carbon atoms or a cycloalkyl group having 3 to 8 carbon atoms, $R^6$, $R^7$, $R_9$, $R^{10}$, $R_{12}$ and $R^{13}$ are each independently a hydrogen atom, an alkyl group having 1 to 8 carbon atoms or a cycloalkyl group having 3 to 6 carbon atoms,

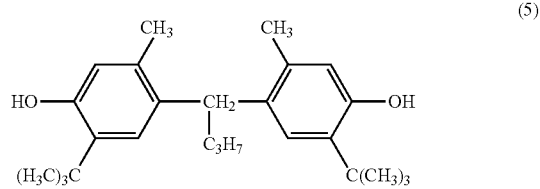

-continued

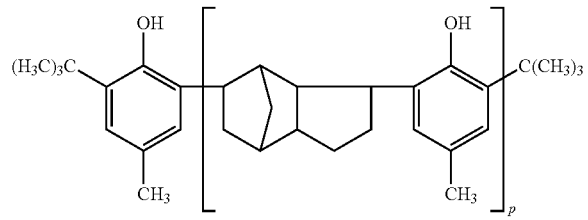

(6)

wherein p is 1 or 2.

8. The thermal recording material according to claim 7, wherein the compound represented by the formula (3) is a compound represented by the following formula (4):

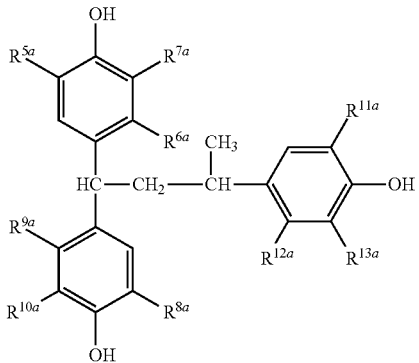

(4)

wherein $R^{5a}$, $R^{8a}$ and $R^{11a}$ are each a tert-butyl group or a cyclohexyl group, $R^{6a}$, $R^{9a}$, and $R^{12a}$ are methyl groups, and $R^{7a}$, $R^{10a}$ and $R^{13a}$ are hydrogen atoms.

9. A phenolsulfonic acid aryl ester, which is represented by the following formula (2):

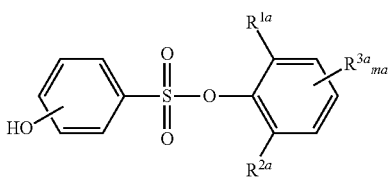

(2)

wherein $R^{1a}$ and $R^{2a}$ are each independently a hydrogen atom, an alkyl group having 1 to 8 carbon atoms, an alkoxy group having 1 to 8 carbon atoms, and $R^{1a}$ and $R^{2a}$ are not simultaneously hydrogen atoms; $R^{3a}$ is an alkyl group having 1 to 8 carbon atoms, an alkenyl group having 2 to 8 carbon atoms, an alkoxy group having 1 to 8 carbon atoms, a halogen atom, a nitro group, a hydroxy group, a cyano group, an aryl group having 6 to 14 carbon atoms or an aralkyl group having 7 to 15 carbon atoms; and ma is an integer of 0-3.

10. A developer for a thermal recording material, comprising at least one kind of the phenolsulfonic acid aryl ester according to claim 9.

11. A thermal recording material comprising a support and a thermal recording layer comprising a colorless or pale-colored basic leuco dye and a developer for color development of the basic leuco dye, which layer is laminated on at least one surface of the support, wherein the developer contains at least one kind of phenolsulfonic acid aryl ester according to claim 9.

12. The thermal recording material according to claim 11, wherein the developer further contains at least one kind of a second developer selected from the group consisting of a bisphenol compound, a bisphenol sulfone compound, a urea compound and a novolac type phenol compound.

13. The thermal recording material according to claim 11, wherein the thermal recording layer contains at least one kind of sensitizer selected from the group consisting of 1,2-di-(3-methylphenoxy)ethane, fatty acid amide having 10 to 21 carbon atoms, β-benzyloxynaphthalene and diaphenylsulfone.

14. The thermal recording material according to claim 11, wherein the thermal recording layer contains a hindered phenol compound.

15. The thermal recording material according to claim 14, wherein the hindered phenol compound is at least one kind selected from the group consisting of a compound represented by the following formula (3), a compound represented by the following formula (5) and a compound represented by the following formula (6):

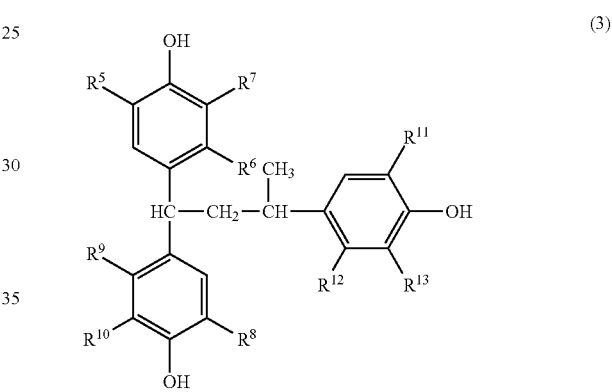

(3)

wherein $R^5$, $R^8$, and $R^{11}$ are each independently an alkyl group having 1 to 8 carbon atoms or a cycloalkyl group having 3 to 8 carbon atoms, $R^6$, $R^7$, $R^9$, $R^{10}$, $R^{12}$ and $R^{13}$ are each independently a hydrogen atom, an alkyl group having 1 to 8 carbon atoms or a cycloalkyl group having 3 to 6 carbon atoms,

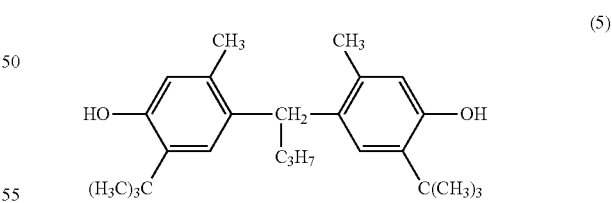

(5)

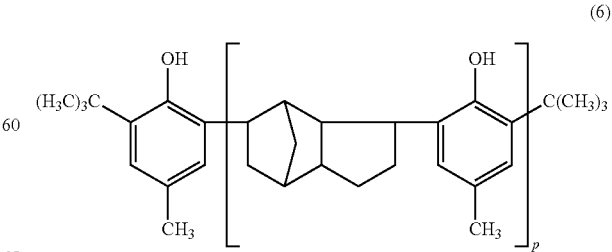

(6)

wherein p is 1 or 2.

16. The thermal recording material according to claim 15, wherein the compound represented by the formula (3) is a compound represented by the following formula (4):
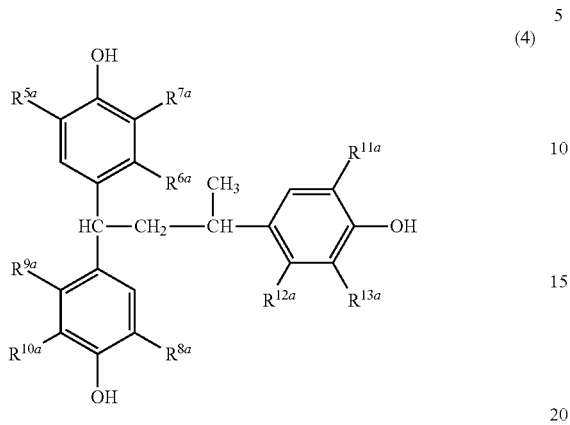
(4)
wherein $R^{5a}$, $R^{8a}$ and $R^{11a}$ are each a tert-butyl group or a cyclohexyl group, $R^{6a}$, $R^{9a}$ and $R^{12a}$ are methyl groups, and $R^{7a}$, $R^{10a}$ and $R^{13a}$ are hydrogen atoms.
* * * * *